(12) United States Patent
Klein et al.

(10) Patent No.: US 9,376,405 B2
(45) Date of Patent: Jun. 28, 2016

(54) BIS-(TRIAZINYLAMINO)-STILBENE DERIVATIVES

(75) Inventors: Cedric Klein, Herrlisheim-Près-Colmar (FR); Frederic Reveaud, Mulhouse (FR); Andrew Clive Jackson, Muenchenstein BL (CH); David Atkinson, Arlesheim BL (CH)

(73) Assignee: CLARIANT INTERNATIONAL LTD, Muttenz (CH)

( * ) Notice: Subject to any disclaimer, the term of this patent is extended or adjusted under 35 U.S.C. 154(b) by 250 days.

(21) Appl. No.: 14/113,686

(22) PCT Filed: Apr. 17, 2012

(86) PCT No.: PCT/EP2012/001648
§ 371 (c)(1),
(2), (4) Date: Feb. 7, 2014

(87) PCT Pub. No.: WO2012/146353
PCT Pub. Date: Nov. 1, 2012

(65) Prior Publication Data
US 2014/0142305 A1    May 22, 2014

(30) Foreign Application Priority Data
Apr. 27, 2011  (EP) .................................. 11003442

(51) Int. Cl.
*C07D 251/68* (2006.01)
*C11D 3/42* (2006.01)
*D21H 21/30* (2006.01)
*C07D 251/54* (2006.01)
*C07D 251/44* (2006.01)
*C07D 251/50* (2006.01)

(52) U.S. Cl.
CPC ............ *C07D 251/54* (2013.01); *C07D 251/44* (2013.01); *C07D 251/50* (2013.01); *C07D 251/68* (2013.01); *C11D 3/42* (2013.01); *D21H 21/30* (2013.01)

(58) Field of Classification Search
CPC ......... C07D 251/68; C11D 3/42; D21H 21/30
USPC ................. 544/193, 193.2; 514/245
See application file for complete search history.

(56) References Cited

U.S. PATENT DOCUMENTS 6,596,864 B1    7/2003  Vogt et al.

FOREIGN PATENT DOCUMENTS

| DE | 2335570 | 1/1974 |
|----|---------|--------|
| GB | 997175  | 7/1965 |
| GB | 1051986 | 12/1966 |

OTHER PUBLICATIONS

International Search Report for PCT/EP2012/001648 Mailed Aug. 30, 2012.

*Primary Examiner* — Venkataraman Balasubramanian
(74) *Attorney, Agent, or Firm* — McBee Moore Woodward Vanik IP, LLC

(57) ABSTRACT

The instant invention relates to novel water soluble bis-(triazinylamino)-stilbene optical brightening agents, a process for their preparation and their use for whitening natural and synthetic materials.

20 Claims, No Drawings

BIS-(TRIAZINYLAMINO)-STILBENE DERIVATIVES

CROSS REFERENCE TO RELATED APPLICATIONS

This application is a §371 National Stage Application of PCT/EP2012/001648, filed Apr. 17, 2012, which claims priority to European Application No. 11003442.8, filed Apr. 27, 2011.

BACKGROUND OF THE INVENTION

1. Field of the Invention

Optical brightening agents (OBAs) of the bis-(triazinylamino)-stilbene type are widely used to brighten natural and regenerated cellulosic fibres, natural and synthetic polyamide and polyurethane fibres, natural or synthetic pigment preparations, textiles and paper.

2. Description of Related Art

The use of high concentrations of optical brightening agents in coating applications can lead to the substrate taking on a greenish hue, particularly in cases where the coating formulation contains no synthetic binder.

One method which has been used to overcome this problem is to use a coating formulation containing a high proportion of a carrier such as a polyethylene glycol.

DE-2 335 570 A1 discloses bis-(triazinylamino)-stilbene derivatives in which both triazinyl radicals are directly substituted by polyethylene glycols. However, only short chains containing from 1 to 3 ethoxylated units are reported.

U.S. Pat. No. 6,596,864 B1 discloses bis-(triazinylamino)-stilbene derivatives in which both triazinyl radicals are substituted by polyethylene glycols having up to 35 ethoxylated units.

GB-997 175 A discloses bis-(triazinylamino)-stilbene derivatives in which both triazinyl radicals are substituted by polyetheramines. However, only short chains containing from 1 to 4 ethoxylated units are reported.

SUMMARY

It has now been found that it is possible to make a new class of bis-(triazinylamino)-stilbene based OBAs that are substituted at the triazine rings with high molecular weight polyetheramines which provide a substantially improved performance, particularly in coating applications with no secondary binder.

The present invention therefore provides optical brightening agents of formula (I)

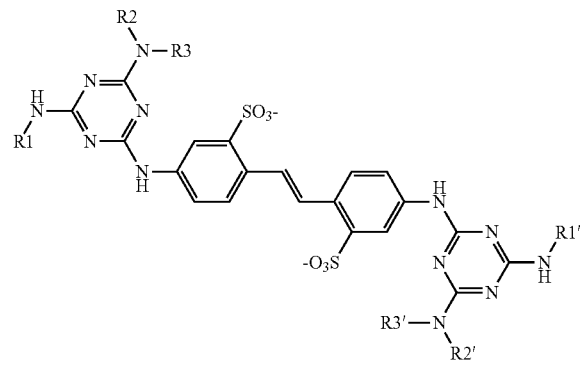

(I)

in which the anionic charge on the brightener is balanced by a cationic charge composed of one or more identical or different cations selected from the group consisting of hydrogen, an alkali metal cation, alkaline earth metal, ammonium, ammonium which is mono-, di-, tri- or tetrasubstituted by a $C_1$-$C_4$ linear or branched alkyl radical, ammonium which is mono-, di-, tri- or tetrasubstituted by a $C_1$-$C_4$ linear or branched hydroxyalkyl radical, ammonium which is, di-, tri- or tetra-substituted by a mixture of $C_1$-$C_4$ linear or branched alkyl radical and linear or branched hydroxyalkyl radical or mixtures of said compounds, R1 and R1' may be the same or different and signify a radical of formula (II)

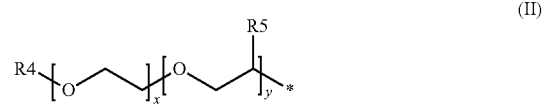

(II)

or R1 together with R1' signify a radical of formula (III)

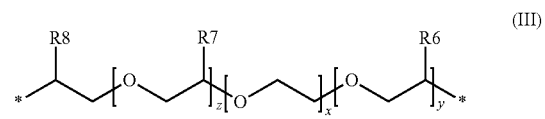

(III)

or R1 together with R1' signify a radical of formula (IV)

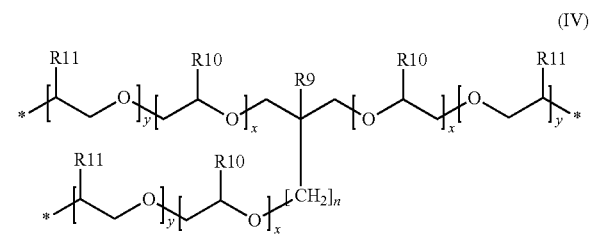

(IV)

or mixtures of said compounds

R2 and R2' may be the same or different and are selected from the group consisting of hydrogen, $C_1$-$C_4$ linear or branched alkyl, $C_2$-$C_4$ linear or branched hydroxyalkyl, —$CH_2CO_2^-$, —$CH_2CH_2CONH_2$ or —$CH_2CH_2CN$, or R2 and R2' signify a radical of formula (II)
or R2 together with R2' signify a radical of formula (III),
or R2 together with R2' signify a radical of formula (IV),
or R2 and R2' signify a radical of formula (V),

(V)

or mixtures of said compounds

R3 and R3' may be the same or different and are selected from the group consisting of hydrogen, $C_1$-$C_4$ linear or branched alkyl, $C_2$-$C_4$ linear or branched hydroxyalkyl, —$CH_2CO_2^-$, —$CH(CO_2^-)CH_2CO_2^-$, —$CH(CO_2^-)CH_2CH_2CO_2^-$, —$CH_2CH_2SO_3^-$, —$CH_2CH_2CO_2^-$, —$CH_2CH(CH_3)CO_2^-$, benzyl, or mixtures of said compounds, or R2 and R3 and/or R2' and R3' together with the neighboring nitrogen atom signify a morpholine, a piperidine, a piperazine, a pyrrole, or a pyrrolidine ring or mixtures of said compounds R12 and R13 may be the same or different and are selected from the group consisting of hydrogen, $C_1$-$C_6$ linear or branched alkyl radical, halogen, —$SR14$, —$OR15$, —$NR16R17$, —$CONR18R19$, —$COR20$, —$SO2NR21R22$, —$CN$, —$CO_2^-$, —$SO_3^-$ or mixtures of said compounds R4, R5, R6, R7, R8, R9, R10, R11, R14, R15, R16, R17, R18, R19, R20, R21 and R22 may be the same or different and are selected from the group consisting of hydrogen, phenyl or $C_1$-$C_{25}$ linear or branched alkyl radical, R5, R6, R7, R8, R10 and R11 are preferred to be $CH_3$ or H and are especially preferred to be $CH_3$ or mixtures of said compounds, x, y and z may be the same or different and are each in the range of from 0 to 200 with the proviso that $x+y+z \geq 5$ n may be in the range of from 0 to 4 or mixtures of said compounds.

DETAILED DESCRIPTION OF A PREFERRED EMBODIMENT

Preferred compound of formula (I) are those in which the anionic charge on the brightener is balanced by a cationic charge composed of one or more identical or different cations selected from the group consisting of hydrogen, Li, Na, K, Ca, Mg, ammonium, ammonium which is mono-, di-, tri- or tetrasubstituted by a $C_1$-$C_4$ linear or branched alkyl radical, ammonium which is mono-, di-, tri- or tetrasubstituted by a $C_1$-$C_4$ linear or branched hydroxyalkyl radical, ammonium which is, di-, tri- or tetrasubstituted by a mixture of $C_1$-$C_4$ linear or branched alkyl radical and linear or branched hydroxyalkyl radical or mixtures of said compounds, R1 and R1' may be the same or different and signify a radical of formula (II)

or R1 together with R1' signify a radical of formula (III)

or R1 together with R1' signify a radical of formula (IV)

or mixtures of said compounds

R2 and R2' may be the same or different and are selected from the group consisting of hydrogen, methyl, ethyl, propyl, butyl, isopropyl, isobutyl, 2-hydroxyethyl, 2-hydroxypropyl, —$CH_2CO_2^-$, —$CH_2CH_2CONH_2$ or —$CH_2CH_2CN$, or R2 and R2' signify a radical of formula (II)

or R2 together with R2' signify a radical of formula (III)

or R2 together with R2' signify a radical of formula (IV)

or R2 and R2' signify a radical of formula (V), or mixtures of said compounds

R3 and R3' may be the same or different and are selected from the group consisting of hydrogen, methyl, ethyl, propyl, butyl, isopropyl, isobutyl, 2-hydroxyethyl, 2-hydroxypropyl, —$CH_2CO_2^-$, —$CH(CO_2^-)CH_2CO_2^-$, —$CH(CO_2^-)CH_2CH_2CO_2^-$, —$CH_2CH_2SO_3^-$, —$CH_2CH_2CO_2^-$, —$CH_2CH(CH_3)CO_2^-$, benzyl, or mixtures of said compounds, or R2 and R3 and/or R2' and R3' together with the neighboring nitrogen atom signify a morpholine, a piperidine or a pyrrolidine ring or mixtures of said compounds R12 and R13 may be the same or different and are selected from the group consisting of hydrogen, methyl, ethyl, propyl, isopropyl, butyl, isobutyl, 2-ethylhexyl, F, Cl, Br, I, —$SR14$, —$OR15$, —$NR16R17$, —$CONR18R19$, —$COR20$, —$SO2NR21R22$, —$CN$, —$CO_2^-$, —$SO_3^-$ or mixtures of said compounds R4, R5, R6, R7, R8, R9, R10, R11, R14, R15, R16, R17, R18, R19, R20, R21 and R22 may be the same or different and are selected from the group consisting of hydrogen, phenyl or $C_1$-$C_{20}$ linear or branched alkyl radical R5, R6, R7, R8, R10 and R11 are preferred to be $CH_3$ or H and are especially preferred to be $CH_3$ or mixtures of said compounds, x, y and z may be the same or different and are each in the range of from 0 to 200 with the proviso that $x+y+z \geq 5$ n may be in the range of from 0 to 4 or mixtures of said compounds.

More preferred compound of formula (I) are those in which the anionic charge on the brightener is balanced by a cationic charge composed of one or more identical or different cations selected from the group consisting of hydrogen, Na, K, ammonium, triethanolamine, dimethylaminoethanol or mixtures of said compounds, R1 and R1' may be the same or different and signify a radical of formula (II)

or R1 together with R1' signify a radical of formula (III)

R2 and R2' may be the same or different and are selected from the group consisting of hydrogen, methyl, ethyl, 2-hydroxyethyl, 2-hydroxypropyl, —$CH_2CO_2^-$, —$CH_2CH_2CONH_2$ or —$CH_2CH_2CN$, or R2 and R2' signify a radical of formula (II)

or R2 together with R2' signify a radical of formula (III)

or R2 and R2' signify a radical of formula (V),

R3 and R3' may be the same or different and are selected from the group consisting of methyl, ethyl, 2-hydroxyethyl, 2-hydroxypropyl, —$CH_2CO_2^-$, —$CH(CO_2^-)CH_2CO_2^-$, —$CH_2CH_2SO_3^-$, or mixtures of said compounds, or R2 and R3 and/or R2' and R3' together with the neighboring nitrogen atom signify a morpholine ring R12 and R13 may be the same or different and are selected from the group consisting of hydrogen, —$CO_2^-$, —$SO_3^-$ R4, R5, R6, R7, R8, R9, R10, R11, R14, R15, R16, R17, R18, R19, R20, R21 and R22 may be the same or different and are selected from the group consisting of hydrogen or $C_1$-$C_{20}$ linear or branched alkyl radical R5, R6, R7, R8, R10 and R11 are preferred to be $CH_3$ or H and are especially preferred to be $CH_3$ x, y and z may be the same or different and are each in the range of from 0 to 150 with the proviso that $x+y+z \geq 5$ n may be in the range of from 0 to 4 or mixtures of said compounds.

Especially preferred compound of formula (I) are those in which the anionic charge on the brightener is balanced by a cationic charge composed of one or more identical or different cations selected from the group consisting of Na, K, dimethylaminoethanol or mixtures of said compounds, R1 and R1' signify a radical of formula (II)

or R1 together with R1' signify a radical of formula (III)

R2 and R2' signify a radical of formula (II)

or R2 and R2' signify a radical of formula (V),

R3 and R3' signify hydrogen,

R12 and R13 are selected from the group consisting of hydrogen, —$CO_2^-$, —$SO_3^-$ R4, R5, R6, R7, R8, R9, R10, R11, R14, R15, R16, R17, R18, R19, R20, R21 and R22 are selected from the group consisting of hydrogen or $C_1$-$C_{20}$ linear or branched alkyl radical R5, R6, R7, R8, R10 and R11 are preferred to be $CH_3$ or H and are especially preferred to be $CH_3$ x, y and z may be the same or different and are each in the range of from 0 to 100 with the proviso that $x+y+z \geq 5$ n may be in the range of from 0 to 4 or mixtures of said compounds.

In compounds of formula (I) in which R12 is hydrogen and R13 is $-SO_3^-$, the $-SO_3^-$ group is preferably in the 4-position of the phenyl group.

In compounds of formula (I) in which R12 and R13 are $-SO_3^-$, the $-SO_3^-$ groups are preferably in the 2,5-positions of the phenyl group.

In compounds of formula (I) in which R12 is hydrogen and R13 is $-CO_3^-$, the $-CO_2^-$ groups are preferably in the 4 position of the phenyl group.

Further subject of the invention is a process for the preparation of a compound of formula (I) as defined above, also in all their preferred embodiments, by stepwise reaction of a cyanuric halide with a) a diamine of formula (VI)

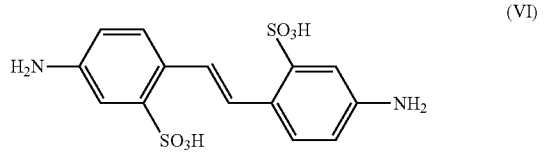 [SMILES: Nc1ccc(/C=C/c2ccc(N)cc2S(=O)(=O)O)c(S(=O)(=O)O)c1]

(VI)

(b) an amine of formula (VII)

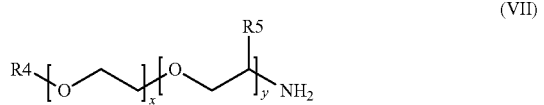

(VII)

or
a diamine of formula (VIII)

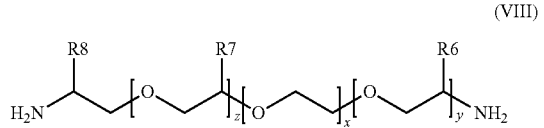

(VIII)

or
a triamine of formula (IX)

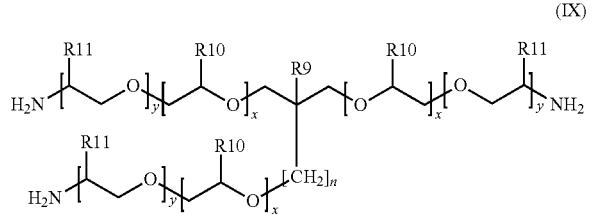

(IX)

or
a mixture of amines of formula (VII) and/or diamines of formula (VIII) and/or triamines of formula (IX)
and
(c) an amine of formula (X)

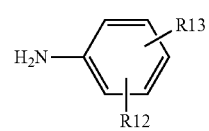

(X)

or
an amine of formula (XI)

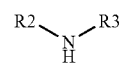

(XI)

or
an amine of formula (VII)
or
a diamine of formula (VIII)
or
a triamine of formula (IX)

R2, R3, R4, R5, R6, R7, R8, R9, R10, R11, R12 and R13 having the same meaning as mentioned above.

As a cyanuric halide there may be employed the fluoride, chloride or bromide. Cyanuric chloride is preferred.

Each reaction may be carried out in an aqueous medium, the cyanuric halide being suspended in water, or in an aqueous/organic medium, the cyanuric halide being dissolved in a solvent such as acetone. Each amine of formula (VII), (X) and (XI), diamine of formula (VI) and (VIII) or triamine of formula (IX) may be introduced without dilution, or in the form of an aqueous solution or suspension.

Compounds of formula (VI), (VII), (VIII), (IX), (X) and (XI) can be reacted with the cyanuric halide in any order, although it is preferred to react the aromatic amines first. Compounds of formula (VI), (VII), (VIII), (IX), (X) and (XI) may be reacted stoichiometrically, in default or in excess, with regard to the cyanuric halide.

For substitution of the first halogen of the cyanuric halide by a compound of formula (VI), (VII), (VIII), (IX), (X) or (XI), it is preferred to operate at a temperature in the range of 0 to 20° C. and under acidic to neutral pH conditions, more preferably in the pH range of 2 to 7. For substitution of the second halogen of the cyanuric halide by a compound of formula (VI), (VII), (VIII), (IX), (X) or (XI), it is preferred to operate at a temperature in the range of 20 to 60° C. and under weakly acidic to weakly alkaline conditions, more preferably at a pH in the range of 4 to 8. For substitution of the third halogen of the cyanuric halide by a compound of formula (VI), (VII), (VIII), (IX), (X) or (XI), it is preferred to operate at a temperature in the range of 60 to 102° C. and under weakly acidic to alkaline conditions, more preferably at a pH in the range of 7 to 10.

The reaction time for substitution of the first, the second and the third halogen of the cyanuric halide by a compound of formula (VI), (VII), (VIII), (IX), (X) or (XI) is in the range of from 10 minutes to 24 hours, preferably of from 30 minutes to 10 hours, more preferably of from 1 to 5 hours.

The pH of each reaction is generally controlled by addition of a suitable base (B), the choice of base (B) being dictated by the desired final composition of the compound of formula (I). Preferred bases (B) are, for example, alkali metal or alkaline earth metal (e.g. lithium, sodium, potassium, calcium, magnesium) hydroxides, carbonates or bicarbonates, or aliphatic tertiary amines, e.g. triethylamine, triethanolamine, triisopropanolamine, dimethylaminoethanol or combinations thereof. Where base (B) is a combination of two or more different bases, the bases may be added in any order, or at the same time.

The base (B) neutralizes the hydrogen halide released during the substitution of cyanuric halide by a compound of formula (VI), (VII), (VIII), (IX), (X) or (XI) and forms a salt (SA), for example according to equation 1 in which base (B) is sodium hydroxide.

$$NaOH + HCl \rightarrow NaCl + H_2O \quad \text{(equation 1)}$$

Where it is necessary to adjust the reaction pH downwards, acids may be employed, examples of which include hydrochloric acid, sulphuric acid, formic acid and acetic acid.

It has been found that compounds of formula (I) exhibit outstanding optical brightening characteristics.

A further subject of the invention therefore is the use of compounds of formula (I) as defined above, also in all their preferred embodiments, as optical brightening agents, preferably for optical brightening of natural and regenerated cellulosic fibres, natural and synthetic polyamide and polyurethane fibres, natural or synthetic pigment preparations, textiles and paper.

For the optical brightening of textiles and non-wovens, compounds of formula (I) may, for example, be employed in padding processes, where the brightener concentration in the treatment bath may be kept almost constant. In the finishing of textiles (fabrics or, preferably, non-woven fabrics) with binding agents, especially synthetic resins, compounds of formula (I) may be added to the synthetic resin either in the treatment bath or before. The optical brightener may be fixed, and the finishing agent cross-linked, in accordance with the cold dwell process or by heat treatment, optionally after intermediate drying. Owing to their stability towards acids and salts, e.g. magnesium chloride and zinc chloride, compounds of formula (I) are also suitable for the optical brightening and simultaneous crease-proof finishing of cotton. Compounds of formula (I) may be employed in an amount in the range of 0.00001 to 5% by weight, preferably 0.00002 to 5% by weight, the % by weight based on the weight of the dry cellulosic substrate.

The compounds of formula (I) are particularly effective when used as optical brightening agents for paper. They may be applied to paper either by addition to a paper stock prior to sheet formation or they may be incorporated into a coating or a sizing composition which are subsequently applied to a paper sheet.

Compounds of formula (I) are more preferably suitable as optical brightening agents for the brightening of paper and non-wovens, even more preferably for optical brightening of paper after sheet formation, or of non-wovens after web formation.

Even more preferably, compounds of formula (I) are suitable for the brightening of paper after sheet formation. This may be effected by adding compounds of formula (I) to a sizing composition or to a pigmented coating composition. The paper may be of fine or coarse nature, and of bleached or unbleached cellulose.

For the treatment of paper in the size-press, sizing solutions or suspensions containing compounds of formula (I) in the range of 0.0001 to 125 grams per liter of sizing solution or suspension, preferably 0.0005 to 100 grams per liter may be used. The sizing solution or suspension may also contain one or more binding agents in a concentration of between 1 and 30% by weight, preferably between 2 and 20% by weight, most preferably between 5 and 15% by weight, the % by weight based on the weight of the sizing solution. The pH of the sizing solution or suspension is typically in the range 5-9, preferably 6-8.

The binding agent is selected from the group consisting of native starch, enzymatically modified starch, chemically modified starch and mixtures thereof. Modified starches are preferably oxidized starch, hydroxyethylated starch or acetylated starch. The native starch is preferably an anionic starch, a cationic starch, or an amphoteric starch. While the starch source may be any, preferably the starch sources are corn, wheat, potato, rice, tapioca or sago.

The concentration of binders in the sizing composition may be between 1 and 30% by weight, preferably between 2 and 20% by weight, most preferably between 5 and 15% by weight, % by weight based on the total weight of the sizing composition.

The sizing solution or suspension may optionally contain a divalent metal salt or a mixture of divalent metal salts differing from the inorganic salts (SA) generated during the synthesis of compounds of formula (I) in a concentration of between 1 and 100 WI, preferably between 2 and 80 WI, most preferably between 5 and 70 WI sizing solution.

Preferred divalent metal salts are selected from the group consisting of calcium chloride, magnesium chloride, calcium bromide, magnesium bromide, calcium iodide, magnesium iodide, calcium nitrate, magnesium nitrate, calcium formate, magnesium formate, calcium acetate, magnesium acetate, calcium citrate, magnesium citrate, calcium gluconate, magnesium gluconate, calcium ascorbate, magnesium ascorbate, calcium sulphite, magnesium sulphite, calcium bisulphite, magnesium bisulphite, calcium dithionite, magnesium dithionite, calcium sulphate, magnesium sulphate, calcium thiosulphate, magnesium thiosulphate and mixtures of said compounds.

More preferred divalent metal salts are selected from the group consisting of calcium chloride, magnesium chloride, calcium bromide, magnesium bromide, calcium sulphate, magnesium sulphate, calcium thiosulphate, magnesium thiosulphate and mixtures of said compounds.

Especially preferred divalent metal salts are selected from the group consisting of calcium chloride, magnesium chloride, magnesium sulphate and mixtures of said compounds.

When the divalent metal salt is a mixture of one or more calcium salts and one or more magnesium salts, the amount of calcium salts may be in the range of 0.1 to 99.9% by weight based on the total weight of added divalent metal salts.

In addition to compounds of formula (I), the sizing solution or suspension may also contain one or more binders, water and optionally optical brighteners, which are structurally different from compounds of formula (I), and optionally one or more divalent metal salts. The sizing solution or suspension may contain by-products formed during the preparation of the compounds of formula (I) as well as other additives conventionally used for the treatment of cellulosic substrates such as textiles, non-wovens or paper.

Examples of paper additives are secondary binders, antifreezes, biocides, defoamers, wax emulsions, dyes, inorganic salts, preservatives, complexing agents, thickeners, surface sizing agents, cross-linkers, pigments, special resins etc.

The sizing composition is preferably prepared by adding compound of formula (I) and, optionally, the divalent metal salt and/or any other components, to an aqueous solution of the binder, preferably at a temperature of between 20° C. and 90° C.

The sizing composition may be applied to the surface of a paper substrate by any surface treatment method known in the art. Examples of application methods of the sizing composition include size-press applications, calendar size application, tub sizing, coating applications and spraying applications. The preferred method of application of the sizing composition is at the size-press such as puddle size press. A preformed sheet of paper is passed through a two-roll nip which is flooded with the sizing composition. The paper absorbs some of the composition, the remainder being removed in the nip.

The paper substrate contains a web of cellulose fibres which may be sourced from any fibrous plant. Preferably the cellulose fibres are sourced from hardwood and/or softwood. The fibres may be either virgin fibres or recycled fibers, or any combination of virgin and recycled fibres.

More preferably, compounds of formula (I) are suitable when used in coating preparations, even more preferably in coating formulation for paper applications.

For the treatment of paper in coating, the pigmented coating compositions are essentially aqueous compositions that contain at least one binder and one white pigment, in particular an opacifying white pigment, and may additionally contain further additives such as dispersing agents and defoamers.

Although it is possible to produce coating compositions that are free from white pigments, the best white substrates for printing are made using opaque coating compositions that contain 10 to 80% by weight, the % by weight based on the total weight of the opaque coating composition, of white pigment. Such white pigments are generally inorganic pigments, e.g., aluminum silicates (e.g. kaolin, otherwise known as china clay), calcium carbonate (e.g. chalk), titanium dioxide, aluminum hydroxide, barium carbonate, barium sulphate, or calcium sulphate (e.g. gypsum), or mixtures thereof.

The binders in the pigmented coating compositions may be any of those commonly used in the paper industry for the production of coating compositions and may consist of a single binder or of a mixture of primary and secondary binders. The sole or primary binder is preferably a synthetic latex, typically a styrene-butadiene, vinyl acetate, styrene acrylic, vinyl acrylic or ethylene vinyl acetate polymer. The secondary binder may be, e.g., carboxymethylcellulose, casein, soy polymers, or polyvinyl alcohol.

The sole or primary binder is used in an amount typically in the range 5 to 25% by weight, the % by weight based on the total weight of white pigment. The secondary binder is used in an amount typically in the range 0.1 to 10% by weight, the % by weight based on the total weight of white pigment; starch however is typically used in the range 3 to 10% by weight, the % by weight based on the total weight of white pigment.

Compounds of formula (I) in the coating composition may be employed in an amount in the range of 0.00001 to 5% by weight, preferably 0.00005 to 5% by weight, the % by weight based on the weight of the white pigment.

Optionally, one or more other materials can be added to improve further the properties of the coating composition. These might include non-ionic or anionic surfactants, and organic solubilizing aids such as polyethylene glycol, polyvinyl pyrrolidone or urea.

The coating composition may be applied to the substrate by any conventional means, for example by air-knife, blade, brush, roller, coating bar or at the size-press, and the coating is dried at temperatures in the range 50-120° C., and preferably 65-95° C.

The following examples shall demonstrate the instant invention in more details. In the present application, if not indicated otherwise, "parts" means "parts by weight" and "%" means "% by weight".

EXAMPLES

Example 1

185.2 parts of 4,4'-diaminostilbene-2,2'-disulphonic acid are added to 700 parts of water and dissolved with the aid of approx. 130 parts of an aqueous sodium hydroxide solution 30% w/w at approx. 25° C. and a pH of approx. 8 to 9. The so-formed solution is added over a period of approx. 30 minutes to 196 parts of cyanuric chloride dispersed in 250 parts of acetone, 400 parts of water and 500 parts of ice. The temperature is kept below 10° C. using an ice/water bath and the pH is maintained at approx. 3 to 4 by dropping in approx. 136 parts of an aqueous sodium hydroxide solution 30% w/w. After 2 hours, the reaction is complete and the pH is increased to approx. 6.5 to 7.0 by dropping in approx. 2 parts of an aqueous sodium hydroxide solution 30% w/w. The resulting aqueous mixture contains compound of formula (1) at a concentration of approx. 0.200 mol per kg of mixture.

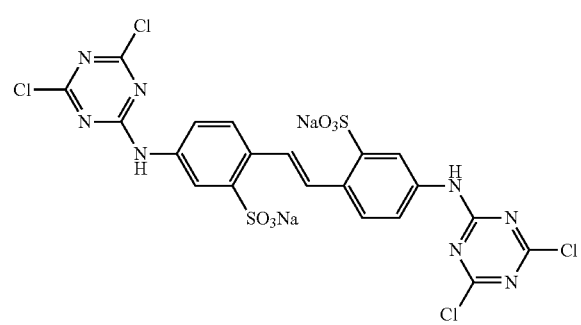

(1)

Example 2

37.2 parts of aniline are added over a period of 30 minutes to 1000 parts of an aqueous mixture prepared according to example 1 and containing approx. 0.200 mol per kg of compound of formula (1). The temperature is kept below 25-30° C. using an ice/water bath and the pH is maintained at approx. 7.0 to 7.5 by dropping in approx. 53 parts of an aqueous sodium hydroxide solution 30% w/w. After 2 hours, the reaction is complete and affords an aqueous mixture contains compound of formula (2) at a concentration of 0.183 mol per kg of mixture.

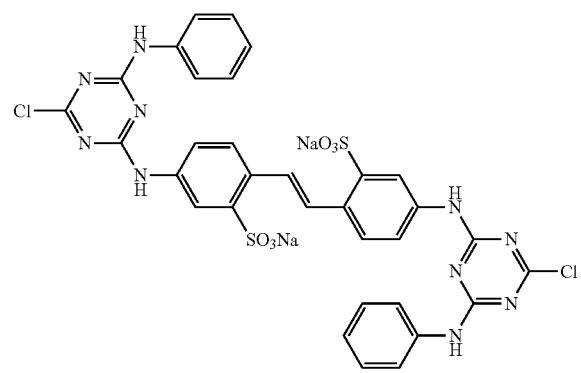

(2)

Example 3

54.9 parts of 4-aminobenzoic acid are added over a period of 30 minutes to 1000 parts of an aqueous mixture prepared according to example 1 and containing approx. 0.200 mol per kg of compound of formula (1). The temperature is increased to 45 to 50° C. using an oil bath the pH is maintained at approx. 7.0 to 7.5 by dropping in approx. 110 parts of an aqueous sodium hydroxide solution 30% w/w. After 2 hours, the reaction is complete and affords an aqueous mixture contains compound of formula (3) at a concentration of 0.171 mol per kg of mixture.

(3)

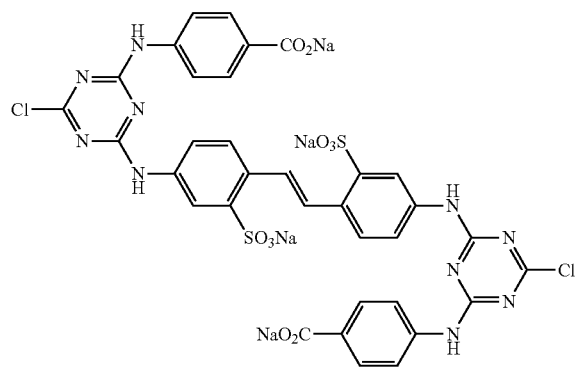

Example 4

291 parts of aniline-4-sulphonic acid are added to 1000 parts of water and dissolved with the aid of approx. 222 parts of an aqueous sodium hydroxide solution 30% w/w at approx. 25° C. and a pH of approx. 8 to 9. The so-formed solution is added over a period of approx. 30 minutes to 305 parts of cyanuric chloride dispersed in 400 parts of water and 600 parts of ice. The temperature is kept below 10° C. using an ice/water bath and by adding into the reaction 900 parts of ice by portions and the pH is maintained at approx. 4 to 5 using approx. 224 parts of an aqueous sodium hydroxide solution 30% w/w until completion of the reaction. Temperature is then increased to 40° C. using an oil bath.

296 parts of 4,4'-diaminostilbene-2,2'-disulphonic acid are added by portions while maintaining a pH of approx. 6.5 to 7.0 using approx. 214 parts of an aqueous sodium hydroxide solution 30% w/w. The temperature is then increased to 65 to 70° C. and the pH maintained at 6.5 to 7.0 using 205 parts of an aqueous sodium hydroxide solution 30% w/w until completion of the reaction. The resulting aqueous mixture contains compound of formula (4) at a concentration of approx. 0.170 mol per kg of mixture.

(4)

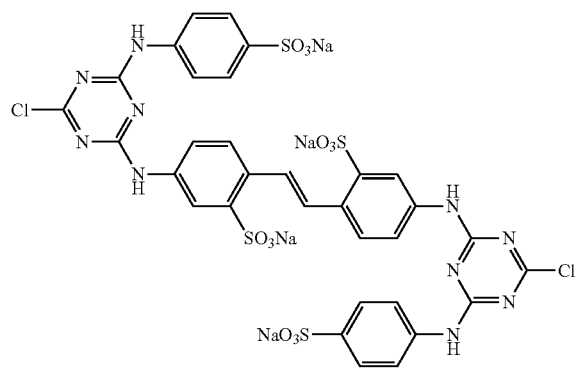

Example 5

520.2 parts of aniline-2,5-disulphonic acid monosodium salt are added to 900 parts of water and dissolved with the aid of approx. 295.1 parts of an aqueous sodium hydroxide solution 30% w/w at approx. 25° C. and a pH of approx. 8 to 9. The so-formed solution is added over a period of approx. 30 minutes to 331.9 parts of cyanuric chloride dispersed in 405 parts of water and 630 parts of ice. The temperature is kept below 5° C. using an ice/water bath and the pH is maintained at approx. 4 to 5 using approx. 504.1 parts of an aqueous sodium carbonate solution 20% w/w. At the end of the addition, the pH is increased to approx. 6 using approx. 35.1 parts of an aqueous sodium carbonate solution 20% w/w and stirring is continued at approx. 0 to 5° C. until completion of the reaction. 151.2 parts of sodium bicarbonate are then added to the reaction mixture. An aqueous solution, obtained by dissolving under nitrogen 333.4 parts of 4,4'-diaminostilbene-2, 2'-disulphonic acid in 1240 parts of water with the aid of approx. 235.8 parts of an aqueous sodium hydroxide solution 30% w/w at approx. 45 to 50° C. and a pH value of approx. 8 to 9, is dropped into the reaction mixture. The resulting mixture is stirred at approx. 45 to 50° C. until completion of the reaction. The resulting aqueous mixture contains compound of formula (5) at a concentration of 0.161 mol per kg of mixture.

(5)

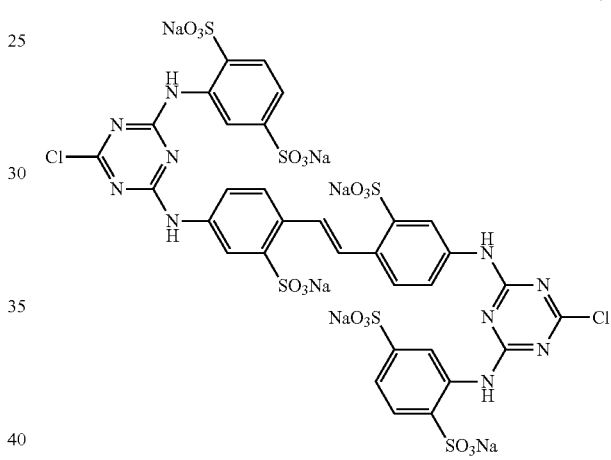

Example 6

294 parts of compound of formula (VIIa)

(VIIa)

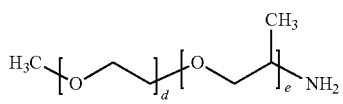

from Clariant and known under the trade name Genamin® M31/700 and having an average molecular weight of 700 g per mol and in which d is approx. 11 in average and e is approx. 3 in average are added over a period of 5 minutes to 1093 parts of an aqueous mixture prepared according to example 2 and containing approx. 0.183 mol per kg of compound of formula (2). The temperature is increased to between 95 and 100° C. while distilling acetone and maintaining the pH at 8.5 by dropping in approx. 54 parts of an aqueous sodium hydroxide solution 30% w/w. After 3 hours, the reaction is complete. The temperature is then decreased to 60° C. and stirring is stopped for 1 hour. Two phases form and the lower layer is separated and filtered while still hot over a sintered glass filter to afford 601 parts of an aqueous solution containing compound of formula (6) at a concentration of approx. 0.310 mol per kg of aqueous solution based on 4,4'-diaminostilbene-2,2'-disulphonic acid.

(6)

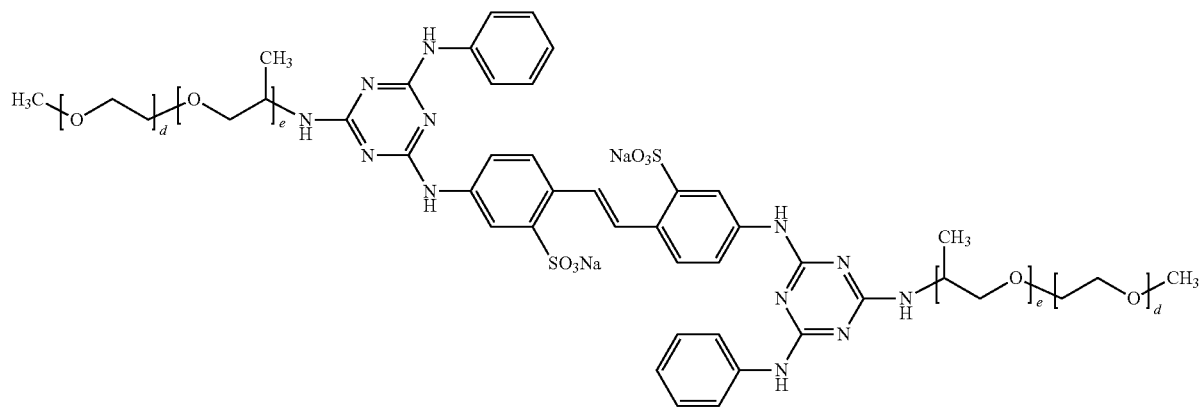

Example 7

840 parts of compound of formula (VIIb)

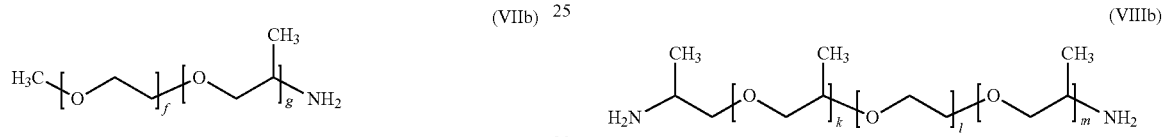
(VIIb)

from Clariant and known under the trade name Genamin® M41/2000 and having an average molecular weight of 2000 g per mol and in which f is approx. 32 in average and g is approx. 9 in average are added over a period of 5 minutes to 1093 parts of an aqueous mixture prepared according to example 2 and containing approx. 0.183 mol per kg of compound of formula (2). The temperature is increased to between 95 and 100° C. while distilling acetone and maintaining the pH at 8.5 by dropping in approx. 53 parts of an aqueous sodium hydroxide solution 30% w/w. After 3 hours, the reaction is complete. The temperature is then decreased to 60° C. and stirring is stopped for 1 hour. Two phases form and the lower layer is separated and filtered while still hot over a sintered glass filter to afford 1478 parts of an aqueous solution containing compound of formula (7) at a concentration of approx. 0.145 mol per kg of aqueous solution based on 4,4'-diaminostilbene-2,2'-disulphonic acid.

Example 8

960 parts of compound of formula (VIIIb)

(VIIIb)

from Clariant and known under the trade name Genamin® D91/4000 and having an average molecular weight of 4000 g per mol and in which k is approx. 3 in average, l is approx. 76 in average and m is approx. 4 in average are added over a period of 5 minutes to 1093 parts of an aqueous mixture prepared according to example 2 and containing approx. 0.183 mol per kg of compound of formula (2). The temperature is increased to between 95 and 100° C. while distilling acetone and maintaining the pH at 8.5 by dropping in approx. 58 parts of an aqueous sodium hydroxide solution 30% w/w. After 3 hours, the reaction is complete. The temperature is then decreased to 60° C. and the resulting solution is filtered while still hot over a sintered glass filter to afford 2433 parts of an aqueous solution containing compound of formula (8) at a concentration of approx. 0.072 mol per kg of aqueous solution based on 4,4'-diaminostilbene-2,2'-disulphonic acid.

(7)

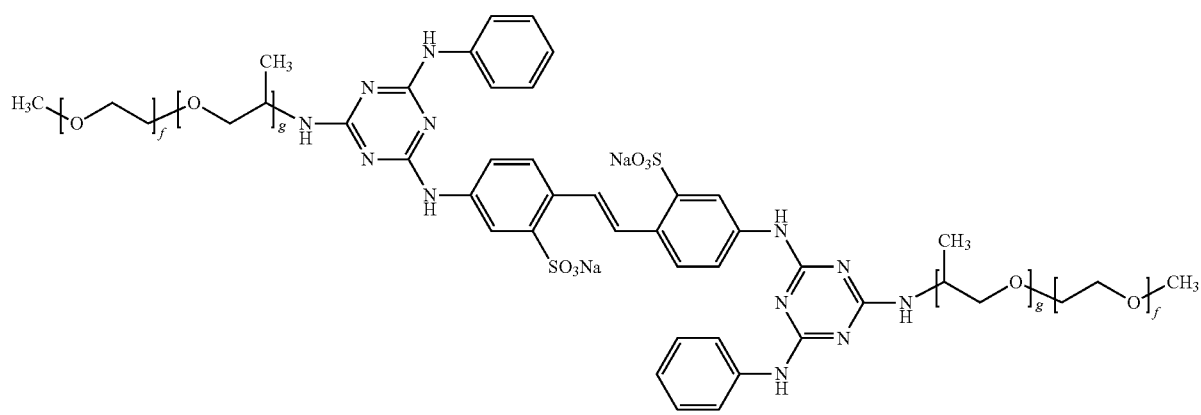

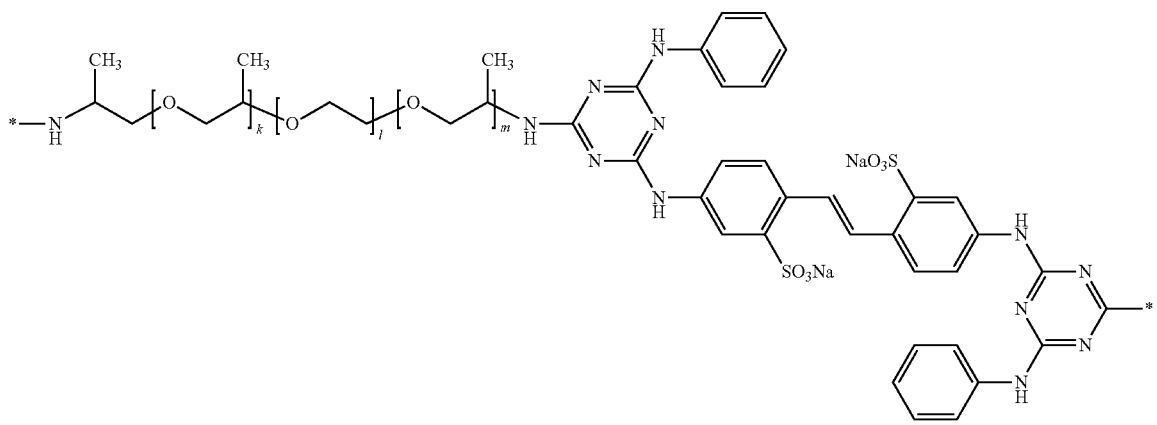

(8)

Example 9

294 parts of compound of formula (VIIa)

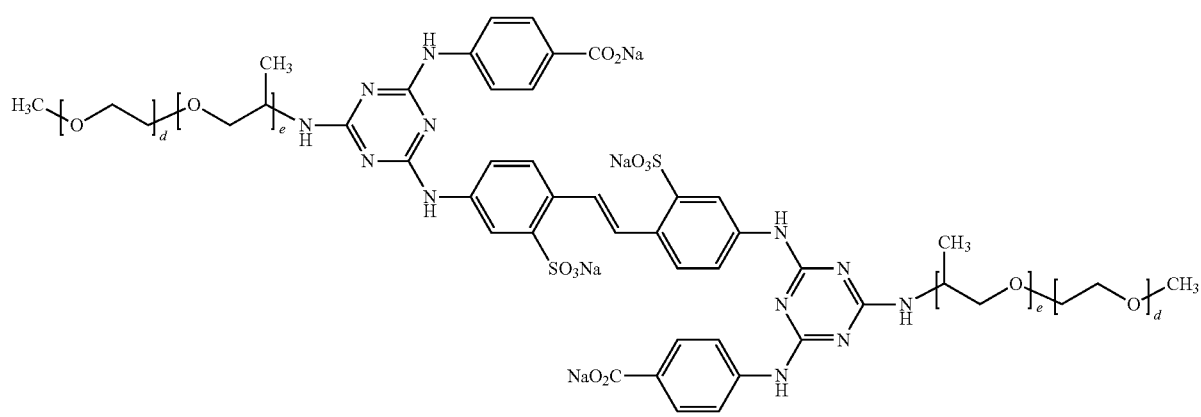

(9)

Example 10

840 parts of compound of formula (VIIb)

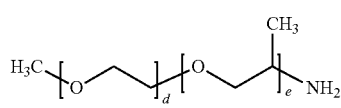

(VIIa)

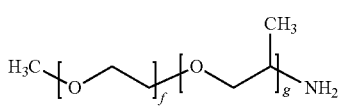

(VIIb)

from Clariant and known under the trade name Genamin® M31/700 and having an average molecular weight of 700 g per mol and in which d is approx. 11 in average and e is approx. 3 in average are added over a period of 5 minutes to 1169 parts of an aqueous mixture prepared according to example 3 and containing approx. 0.171 mol per kg of compound of formula (3). The temperature is increased to between 95 and 100° C. while distilling acetone and maintaining the pH at 8.5 by dropping in approx. 58 parts of an aqueous sodium hydroxide solution 30% w/w. After 3 hours, the reaction is complete. The temperature is then decreased to 60° C. and stirring is stopped for 1 hour. Two phases form and the lower layer is separated and filtered while still hot over a sintered glass filter to afford 1347 parts of an aqueous solution containing compound of formula (9) at a concentration of approx. 0.137 mol per kg of aqueous solution based on 4,4'-diaminostilbene-2,2'-disulphonic acid.

from Clariant and known under the trade name Genamin® M41/2000 and having an average molecular weight of 2000 g per mol and in which f is approx. 32 in average and g is approx. 9 in average are added over a period of 5 minutes to 1169 parts of an aqueous mixture prepared according to example 3 and containing approx. 0.171 mol per kg of compound of formula (3). The temperature is increased to between 95 and 100° C. while distilling acetone and maintaining the pH at 8.5 by dropping in approx. 60 parts of an aqueous sodium hydroxide solution 30% w/w. After 3 hours, the reaction is complete. The temperature is then decreased to 60° C. and stirring is stopped for 1 hour. Two phases form and the lower layer is separated and filtered while still hot over a sintered glass filter to afford 1710 parts of an aqueous solution containing compound of formula (10) at a concentration of approx. 0.112 mol per kg of aqueous solution based on 4,4'-diaminostilbene-2,2'-disulphonic acid.

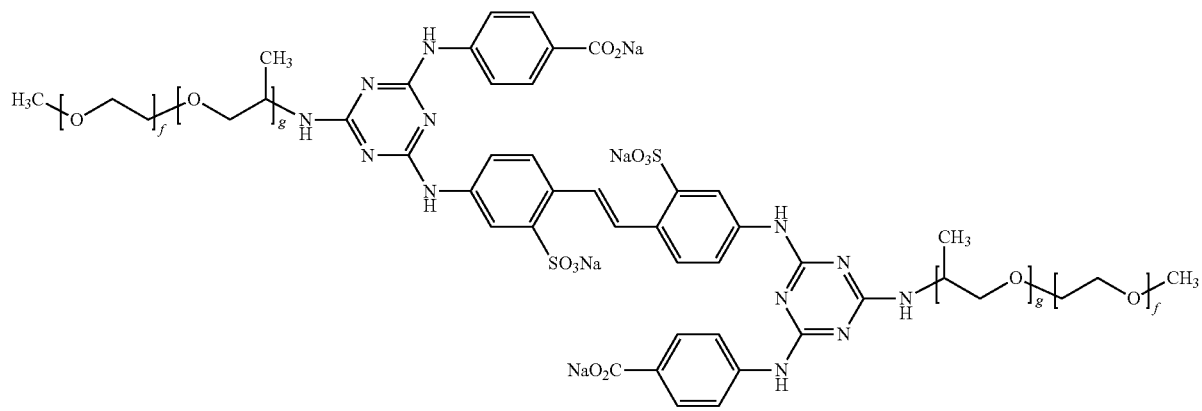

(10)

Example 11
144 parts of compound of formula (VIIIa)

Example 12
294 parts of compound of formula (VIIa)

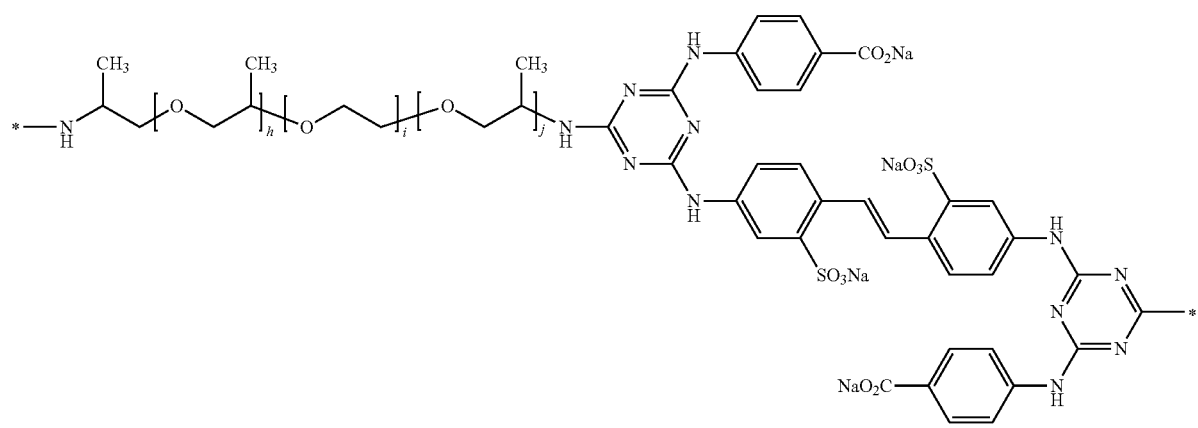

(11)

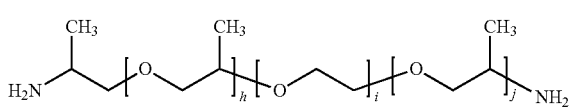

from Clariant and known under the trade name Genamin® D23/600 and having an average molecular weight of 600 g per mol and in which h is approx. 2.5 in average, i is approx. 4.5 in average and i is approx. 3.5 in average are added over a period of 5 minutes to 1169 parts of an aqueous mixture prepared according to example 3 and containing approx. 0.171 mol per kg of compound of formula (3). The temperature is increased to between 95 and 100° C. while distilling acetone and maintaining the pH at 8.5 by dropping in approx. 57 parts of an aqueous sodium hydroxide solution 30% w/w. After 3 hours, the reaction is complete. The temperature is then decreased to 60° C. and stirring is stopped for 1 hour. Two phases form and the lower layer is separated and filtered while still hot over a sintered glass filter to afford 632 parts of an aqueous solution containing compound of formula (11) at a concentration of approx. 0.235 mol per kg of aqueous solution based on 4,4'-diaminostilbene-2,2'-disulphonic acid.

from Clariant and known under the trade name Genamin® M31/700 and having an average molecular weight of 700 g per mol and in which d is approx. 11 in average and e is approx. 3 in average are added over a period of 5 minutes to 1176 parts of an aqueous mixture prepared according to example 4 and containing approx. 0.170 mol per kg of compound of formula (4). The temperature is increased to between 95 and 100° C. while maintaining the pH at 8.5 by dropping in approx. 53 parts of an aqueous sodium hydroxide solution 30% w/w. After 3 hours, the reaction is complete. The temperature is then decreased to 60° C. and stirring is stopped for 1 hour. Two phases form and the lower layer is separated and filtered while still hot over a sintered glass filter to afford 1100 parts of an aqueous solution containing compound of formula (12) at a concentration of approx. 0.171 mol per kg of aqueous solution based on 4,4'-diaminostilbene-2, 2'-disulphonic acid.

(12)

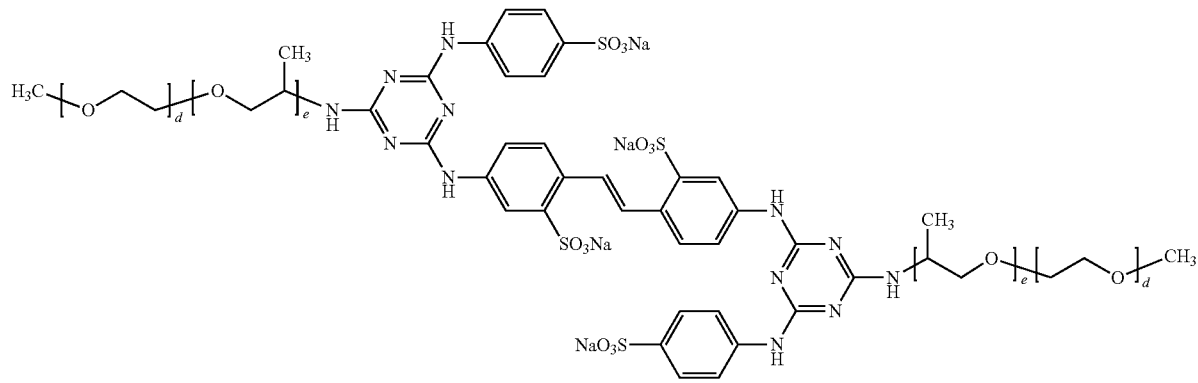

Example 13

840 parts of compound of formula (VIIb)

Example 14

144 parts of compound of formula (VIIIa)

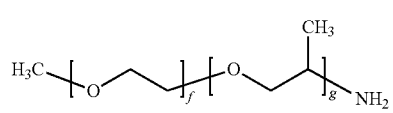

(VIIb)

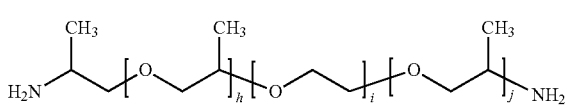

(VIIIa)

from Clariant and known under the trade name Genamin® M41/2000 and having an average molecular weight of 2000 g per mol and in which f is approx. 32 in average and g is approx. 9 in average are added over a period of 5 minutes to 1176 parts of an aqueous mixture prepared according to example 4 and containing approx. 0.170 mol per kg of compound of formula (4). The temperature is increased to between 95 and 100° C. while maintaining the pH at 8.5 by dropping in approx. 52 parts of an aqueous sodium hydroxide solution 30% w/w. After 3 hours, the reaction is complete. The temperature is then decreased to 60° C. and stirring is stopped for 1 hour. Two phases form and the lower layer is separated and filtered while still hot over a sintered glass filter to afford 1650 parts of an aqueous solution containing compound of formula (13) at a concentration of approx. 0.118 mol per kg of aqueous solution based on 4,4'-diaminostilbene-2,2'-disulphonic acid.

from Clariant and known under the trade name Genamin® D23/600 and having an average molecular weight of 600 g per mol and in which h is approx. 2.5 in average, i is approx. 4.5 in average and j is approx. 3.5 in average are added over a period of 5 minutes to 1176 parts of an aqueous mixture prepared according to example 4 and containing approx. 0.170 mol per kg of compound of formula (4). The temperature is increased to between 95 and 100° C. while maintaining the pH at 8.5 by dropping in approx. 53 parts of an aqueous sodium hydroxide solution 30% w/w. After 3 hours, the reaction is complete. The temperature is then decreased to 60° C. and stirring is stopped for 1 hour. Two phases form and the lower layer is separated and filtered while still hot over a sintered glass filter to afford 770 parts of an aqueous solution containing compound of formula (14) at a concentration of approx. 0.238 mol per kg of aqueous solution based on 4,4'-diaminostilbene-2,2'-disulphonic acid.

(13)

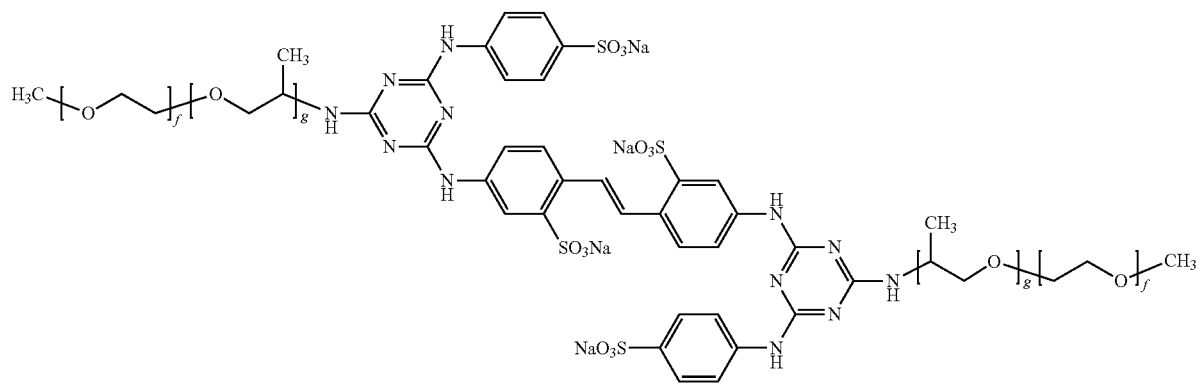

(14)

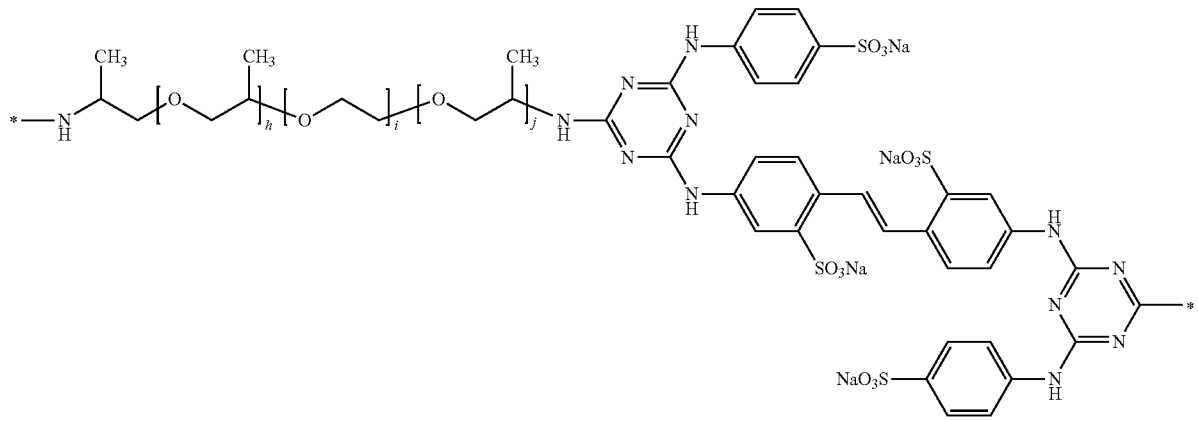

Example 15

960 parts of compound of formula (VIIIb)

Example 16

294 parts of compound of formula (VIIa)

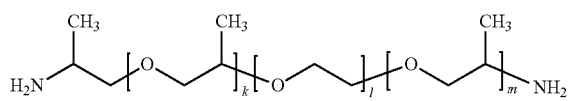
(VIIIb)

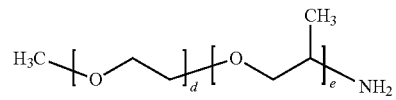
(VIIa)

from Clariant and known under the trade name Genamin® D91/4000 and having an average molecular weight of 4000 g per mol and in which k is approx. 3 in average, l is approx. 76 in average and m is approx. 4 in average are added over a period of 5 minutes to 1176 parts of an aqueous mixture prepared according to example 4 and containing approx. 0.170 mol per kg of compound of formula (4). The temperature is increased to between 95 and 100° C. while maintaining the pH at 8.5 by dropping in approx. 51 parts of an aqueous sodium hydroxide solution 30% w/w. After 3 hours, the reaction is complete. The temperature is then decreased to 60° C. and the resulting solution is filtered while still hot over a sintered glass filter to afford 2150 parts of an aqueous solution containing compound of formula (15) at a concentration of approx. 0.093 mol per kg of aqueous solution based on 4,4'-diaminostilbene-2,2'-disulphonic acid.

from Clariant and known under the trade name Genamin® M31/700 and having an average molecular weight of 700 g per mol and in which d is approx. 11 in average and e is approx. 3 in average are added over a period of 5 minutes to 1242 parts of an aqueous mixture prepared according to example 5 and containing approx. 0.161 mol per kg of compound of formula (5). The temperature is increased to between 95 and 100° C. while maintaining the pH at 8.5 by dropping in approx. 51 parts of an aqueous sodium hydroxide solution 30% w/w. After 3 hours, the reaction is complete. The temperature is then decreased to 60° C. and the resulting solution is filtered while still hot over a sintered glass filter to afford 1533 parts of an aqueous solution containing compound of formula (16) at a concentration of approx. 0.128 mol per kg of aqueous solution based on 4,4'-diaminostilbene-2,2'-disulphonic acid.

(15)

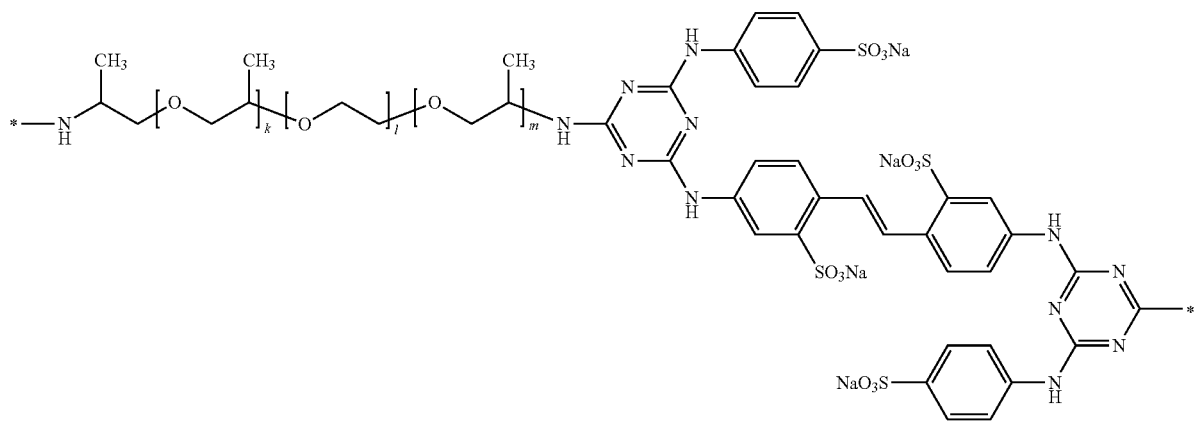

(16)

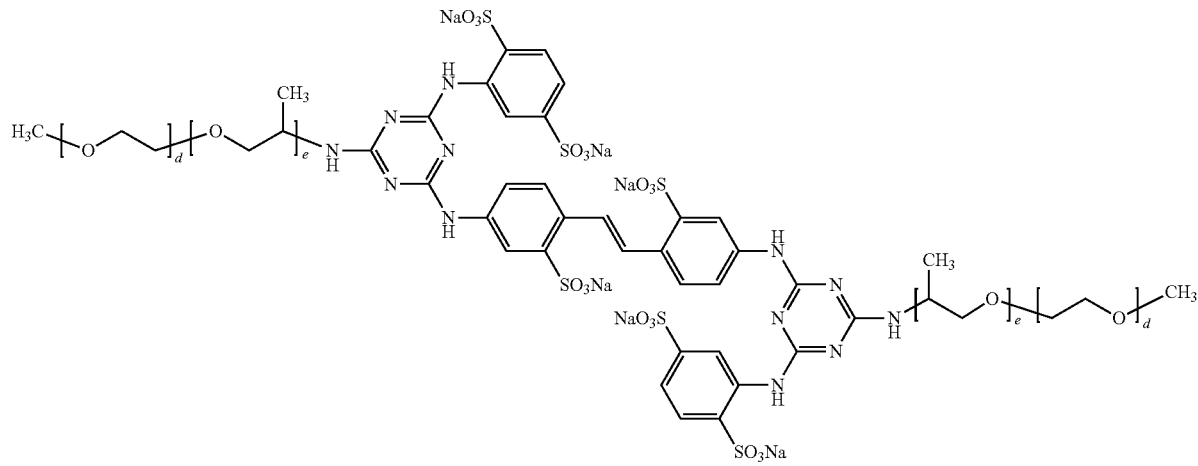

Example 17

840 parts of compound of formula (VIIb)

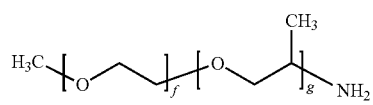

(VIIb)

from Clariant and known under the trade name Genamin® M41/2000 and having an average molecular weight of 2000 g per mol and in which f is approx. 32 in average and g is approx. 9 in average are added over a period of 5 minutes to 1242 parts of an aqueous mixture prepared according to example 5 and containing approx. 0.161 mol per kg of compound of formula (5). The temperature is increased to between 95 and 100° C. while maintaining the pH at 8.5 by dropping in approx. 53 parts of an aqueous sodium hydroxide solution 30% w/w. After 3 hours, the reaction is complete. The temperature is then decreased to 60° C. and stirring is stopped for 1 hour. Two phases form and the lower layer is separated and filtered while still hot over a sintered glass filter to afford 1713 parts of an aqueous solution containing compound of formula (17) at a concentration of approx. 0.114 mol per kg of aqueous solution based on 4,4'-diaminostilbene-2,2'-disulphonic acid.

(17)

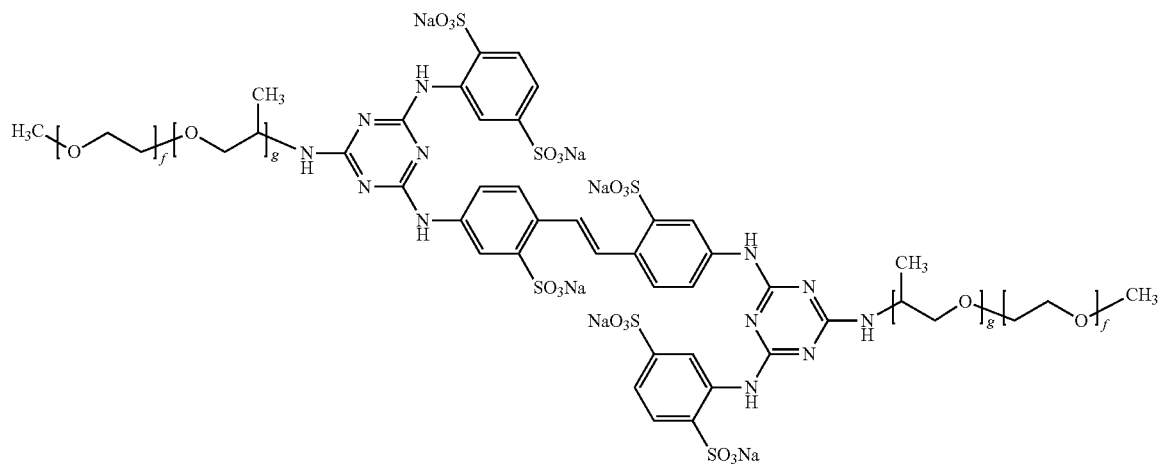

Example 18

144 parts of compound of formula (VIIIa)

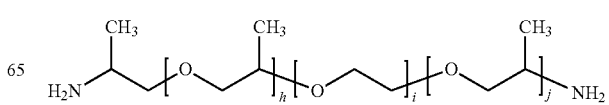

(VIIIa)

from Clariant and known under the trade name Genamin® D23/600 and having an average molecular weight of 600 g per mol and in which h is approx. 2.5 in average, i is approx. 4.5 in average and j is approx. 3.5 in average are added over a period of 5 minutes to 1242 parts of an aqueous mixture prepared according to example 5 and containing approx. 0.161 mol per kg of compound of formula (5). The temperature is increased to between 95 and 100° C. while maintaining the pH at 8.5 by dropping in approx. 54 parts of an aqueous sodium hydroxide solution 30% w/w. After 3 hours, the reaction is complete. The temperature is then decreased to 60° C. and the resulting solution is filtered while still hot over a sintered glass filter to afford 1400 parts of an aqueous solution containing compound of formula (18) at a concentration of approx. 0.143 mol per kg of aqueous solution based on 4,4'-diaminostilbene-2,2'-disulphonic acid.

from Clariant and known under the trade name Genamin® D91/4000 and having an average molecular weight of 4000 g per mol and in which k is approx. 3 in average, l is approx. 76 in average and m is approx. 4 in average are added over a period of 5 minutes to 1242 parts of an aqueous mixture prepared according to example 5 and containing approx. 0.161 mol per kg of compound of formula (5). The temperature is increased to between 95 and 100° C. while maintaining the pH at 8.5 by dropping in approx. 46 parts of an aqueous sodium hydroxide solution 30% w/w. After 3 hours, the reaction is complete. The temperature is then decreased to 60° C. and the resulting solution is filtered while still hot over a sintered glass filter to afford 2150 parts of an aqueous solution containing compound of formula (19) at a concentration of approx. 0.088 mol per kg of aqueous solution based on 4,4'-diaminostilbene-2,2'-disulphonic acid.

(18)

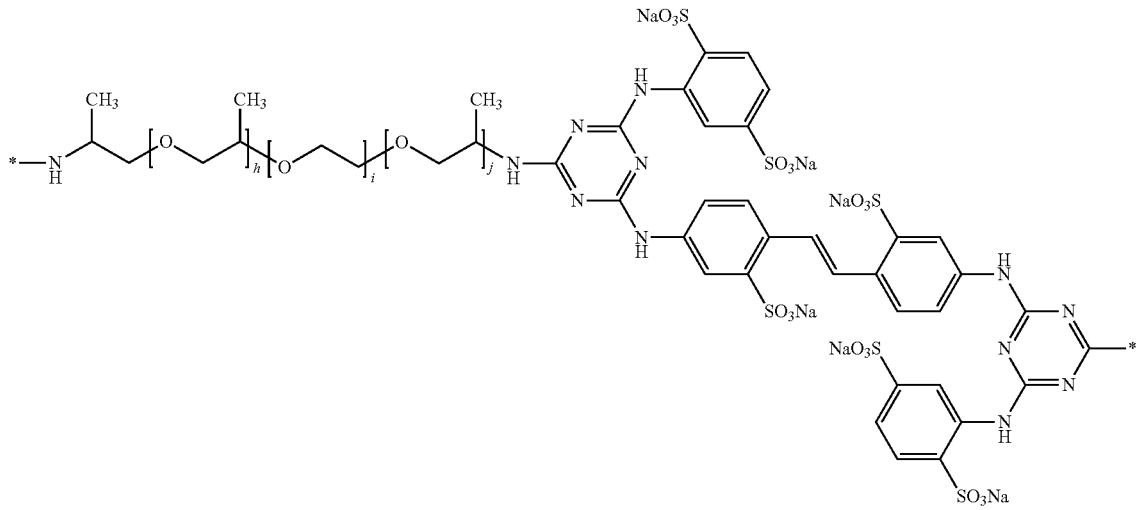

Example 19

960 parts of compound of formula (VIIIb)

(VIIIb)

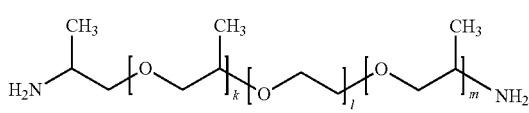

(19)

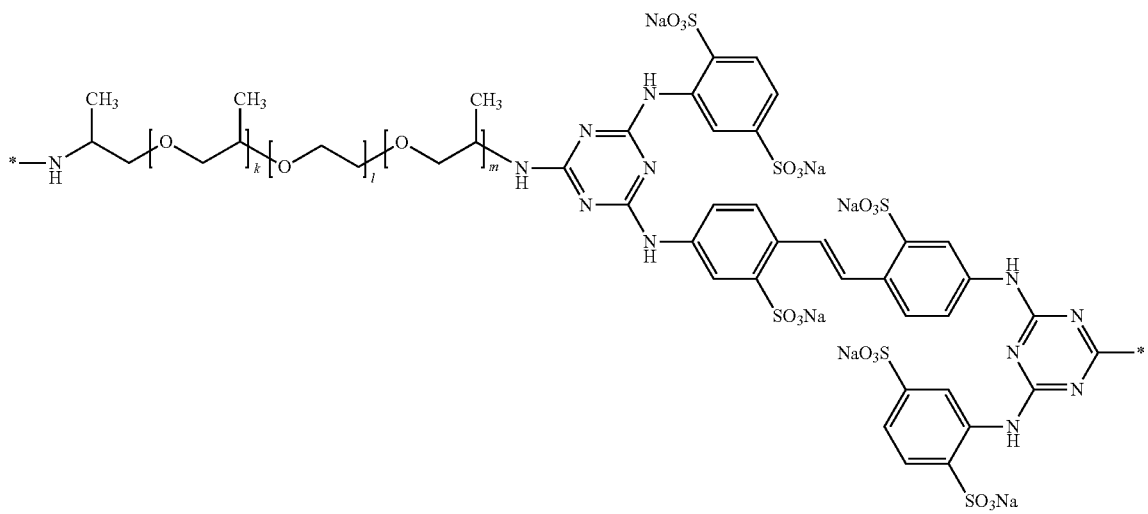

Example 20

588 parts of compound of formula (VIIa)

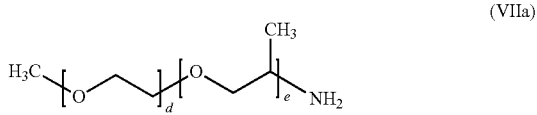

(VIIa)

from Clariant and known under the trade name Genamin® M31/700 and having an average molecular weight of 700 g per mol and in which d is approx. 11 in average and e is approx. 3 in average are added over a period of 5 minutes to 1000 parts of an aqueous mixture prepared according to example 1 and containing approx. 0.200 mol per kg of compound of formula (1). The temperature is increased to between 95 and 100° C. while distilling acetone and maintaining the pH at 8.5 by dropping in approx. 98 parts of an aqueous sodium hydroxide solution 30% w/w. After 3 hours, the reaction is complete. The temperature is then decreased to 60° C. and stirring is stopped for 1 hour. Two phases form and the lower layer is separated and filtered while still hot over a sintered glass filter to afford 996 parts of an aqueous solution containing compound of formula (20) at a concentration of approx. 0.183 mol per kg of aqueous solution based on 4,4'-diaminostilbene-2,2'-disulphonic acid.

per mol and in which d is approx. 11 in average and e is approx. 3 in average are added over a period of 5 minutes to 1000 parts of an aqueous mixture prepared according to example 1 and containing approx. 0.200 mol per kg of compound of formula (1). The temperature is increased to between 45 and 55° C. while maintaining the pH at 7.5 by dropping in approx. 61 parts of an aqueous sodium hydroxide solution 30% w/w. After 3 hours, the reaction is complete.

144 parts of compound of formula (VIIIa)

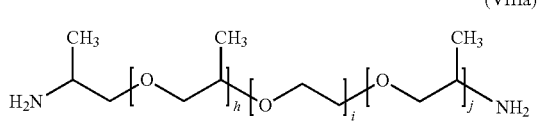

(VIIIa)

from Clariant and known under the trade name Genamin® D23/600 and having an average molecular weight of 600 g per mol and in which h is approx. 2.5 in average, i is approx. 4.5

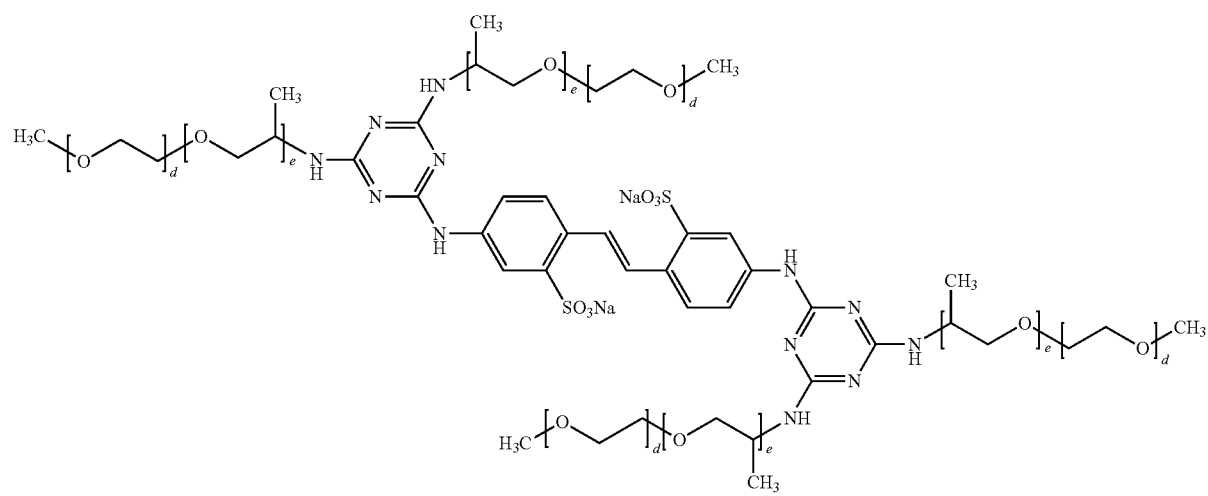

(20)

Example 21

280 parts of compound of formula (VIIa)

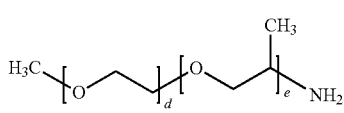

(VIIa)

from Clariant and known under the trade name Genamin® M31/700 and having an average molecular weight of 700 g in average and j is approx. 3.5 in average are added over a period of 5 minutes. The temperature is increased to between 95 and 100° C. while distilling acetone and maintaining the pH at 8.5 by dropping in approx. 49 parts of an aqueous sodium hydroxide solution 30% w/w. After 3 hours, the reaction is complete. The temperature is then decreased to 60° C. and stirring is stopped for 1 hour. Two phases form and the lower layer is separated and filtered while still hot over a sintered glass filter to afford 772 parts of an aqueous solution containing compound of formula (21) at a concentration of approx. 0.230 mol per kg of aqueous solution based on 4,4'-diaminostilbene-2,2'-disulphonic acid.

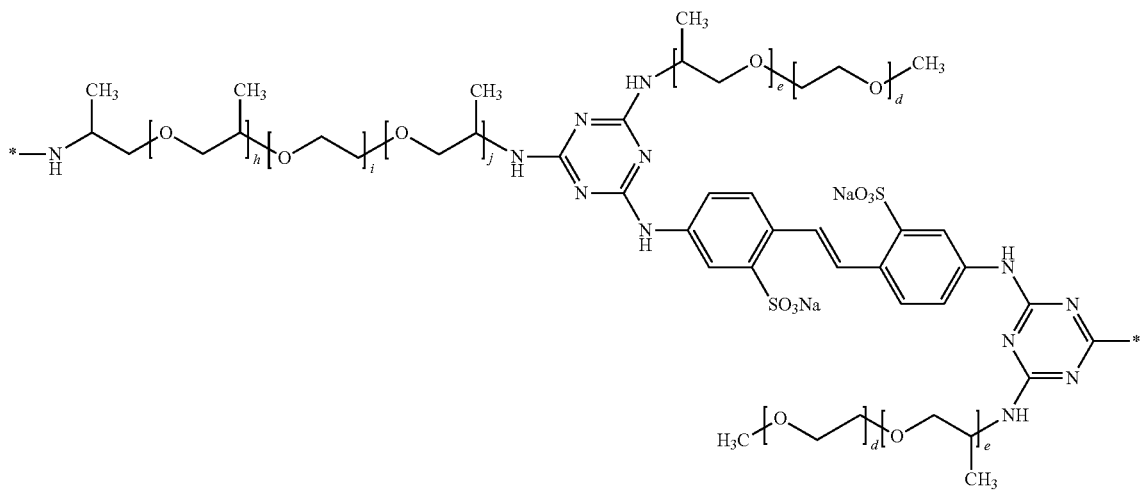
(21)
Comparative Example 1
Comparative aqueous solution (1) is prepared by dissolving compound of formula (50) in water at a concentration of 0.194 mol per kg of aqueous solution.
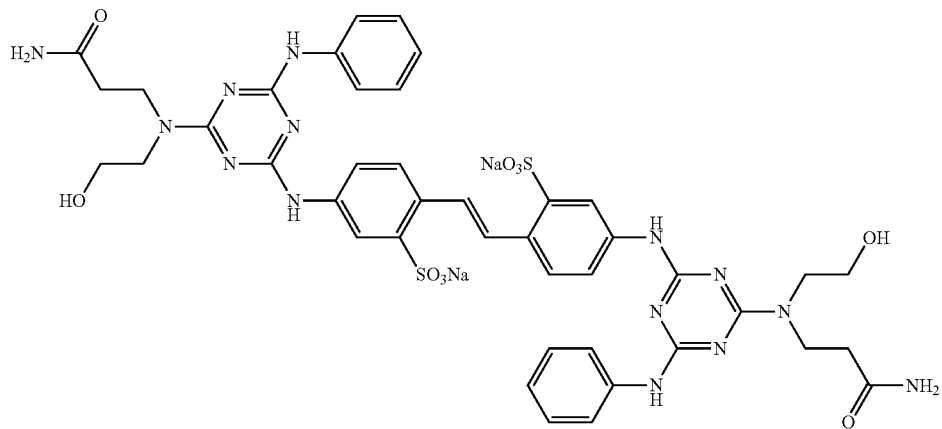
(50)
Comparative Example 2
Comparative aqueous solution (2) is prepared by dissolving compound of formula (51) in water at a concentration of 0.194 mol per kg of aqueous solution.
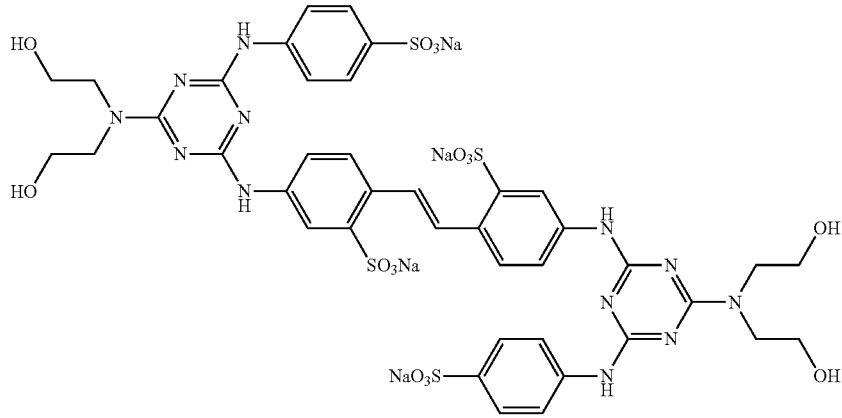
(51)

Application Example 1

A coating composition is prepared containing 7000 parts chalk (commercially available under the trade name Hydrocarb 90 from OMYA), 3000 parts clay (commercially available under the trade name Kaolin SPS from IMERYS), 4280 parts water, 60 parts dispersing agent (a sodium salt of a polyacrylic acid commercially available under the trade name Polysalz S from BASF) and 2000 parts of 50% latex (a styrene butadiene copolymer commercially available under the trade name DL 921 from Dow). The solids content of the coating composition is adjusted to approx. 65% by the addition of water, and the pH is adjusted to 8-9 with sodium hydroxide.

The so-formed coating composition is divided in small portions in which are added with stirring, aqueous solutions containing compounds of formula (6), (7), (8) and (50) respectively prepared according to example 6, 7, 8 and comparative example 1 at a concentration of from 0 to 0.0008 mol per 100 g of dry solid (mol being based on 4,4'-diaminostilbene-2,2'-disulphonic acid).

The brightened coating composition is then applied to a commercial 75 gsm neutral-sized white paper base sheet using an automatic wire-wound bar applicator with a standard speed setting and a standard load on the bar. The coated paper is then dried for 5 minutes in a hot air flow. Afterwards the paper is allowed to condition and measured then for CIE Whiteness on a calibrated Auto-Elrepho spectrophotometer. The results are shown in Table 1 and clearly show that the instant invention provides a higher level of whiteness.

TABLE 1

| Concentration (mol per 100 g of dry solid)* | Whiteness | | | |
|---|---|---|---|---|
| | Compound of formula (6) | Compound of formula (7) | Compound of formula (8) | Compound of formula (50) |
| 0 | 83.6 | 83.6 | 83.6 | 83.6 |
| 0.00006 | 90.1 | 90.4 | 90.5 | 90.0 |
| 0.00012 | 93.5 | 93.9 | 94.8 | 93.3 |
| 0.00017 | 96.0 | 97.4 | 97.9 | 95.7 |
| 0.00029 | 99.4 | 102.9 | 105.3 | 96.8 |
| 0.00039 | 101.6 | 103.9 | 108.4 | 96.9 |
| 0.00058 | 103.8 | 106.3 | 113.0 | 97.3 |
| 0.00078 | 103.3 | 106.8 | 116.5 | 94.6 |

*mol per 100 g of dry solid based on mol of 4,4'-diaminostilbene-2,2'-disulphonic acid per 100 g of dry solid

Application Example 2

A coating composition is prepared containing 7000 parts chalk (commercially available under the trade name Hydrocarb 90 from OMYA), 3000 parts clay (commercially available under the trade name Kaolin SPS from IMERYS), 4280 parts water, 60 parts dispersing agent (a sodium salt of a polyacrylic acid commercially available under the trade name Polysalz S from BASF) and 2000 parts of 50% latex (a styrene butadiene copolymer commercially available under the trade name DL 921 from Dow). The solids content of the coating composition is adjusted to approx. 65% by the addition of water, and the pH is adjusted to 8-9 with sodium hydroxide.

The so-formed coating composition is divided in small portions in which are added with stirring, aqueous solutions containing compounds of formula (12), (13), (15) and (51) respectively prepared according to example 12, 13, 15 and comparative example 2 at a concentration of from 0 to 0.0008 mol per 100 g of dry solid (mol being based on 4,4'-diaminostilbene-2,2'-disulphonic acid).

The brightened coating composition is then applied to a commercial 75 gsm neutral-sized white paper base sheet using an automatic wire-wound bar applicator with a standard speed setting and a standard load on the bar. The coated paper is then dried for 5 minutes in a hot air flow. Afterwards the paper is allowed to condition and measured then for CIE Whiteness on a calibrated Auto-Elrepho spectrophotometer. The results are shown in Table 2 and clearly show that the instant invention provides a higher level of whiteness.

TABLE 2

| Concentration (mol per 100 g of dry solid)* | Whiteness | | | |
|---|---|---|---|---|
| | Compound of formula (12) | Compound of formula (13) | Compound of formula (15) | Compound of formula (51) |
| 0 | 89.5 | 89.5 | 89.5 | 89.5 |
| 0.00006 | 98.4 | 98.2 | 98.5 | 98.0 |
| 0.00012 | 102.0 | 102.1 | 102.1 | 101.8 |
| 0.00017 | 104.8 | 108.3 | 108.0 | 103.3 |
| 0.00029 | 109.2 | 115.1 | 113.6 | 102.5 |
| 0.00039 | 110.9 | 117.5 | 118.0 | 102.0 |
| 0.00058 | 113.5 | 121.8 | 121.7 | 95.4 |
| 0.00078 | 116.0 | 124.5 | 124.4 | 91.3 |

*mol per 100 g of dry solid based on mol of 4,4'-diaminostilbene-2,2'-disulphonic acid per 100 g of dry solid

Application Example 3

A coating composition is prepared containing 7000 parts chalk (commercially available under the trade name Hydrocarb 90 from OMYA), 3000 parts clay (commercially available under the trade name Kaolin SPS from IMERYS), 4280 parts water, 60 parts dispersing agent (a sodium salt of a polyacrylic acid commercially available under the trade name Polysalz S from BASF) and 2000 parts of 50% latex (a styrene butadiene copolymer commercially available under the trade name DL 921 from Dow). The solids content of the coating composition is adjusted to approx. 65% by the addition of water, and the pH is adjusted to 8-9 with sodium hydroxide.

The so-formed coating composition is divided in small portions in which are added with stirring, aqueous solutions containing compounds of formula (9), (10), (11) and (51) respectively prepared according to example 9, 10, 11 and comparative example 2 at a concentration of from 0 to 0.0008 mol per 100 g of dry solid (mol being based on 4,4'-diaminostilbene-2,2'-disulphonic acid).

The brightened coating composition is then applied to a commercial 75 gsm neutral-sized white paper base sheet using an automatic wire-wound bar applicator with a standard speed setting and a standard load on the bar. The coated paper is then dried for 5 minutes in a hot air flow. Afterwards the paper is allowed to condition and measured then for CIE Whiteness on a calibrated Auto-Elrepho spectrophotometer. The results are shown in Table 3 and clearly show that the instant invention provides a higher level of whiteness.

TABLE 3

| Concentration (mol per 100 g of dry solid)* | Whiteness | | | |
|---|---|---|---|---|
| | Compound of formula (9) | Compound of formula (10) | Compound of formula (11) | Compound of formula (51) |
| 0 | 84.4 | 84.4 | 84.4 | 84.4 |
| 0.00006 | 91.7 | 91.6 | 90.8 | 90.5 |
| 0.00012 | 95.6 | 97.4 | 95.5 | 95.2 |

TABLE 3-continued

| Concentration (mol per 100 g of dry solid)* | Whiteness | | | |
|---|---|---|---|---|
| | Compound of formula (9) | Compound of formula (10) | Compound of formula (11) | Compound of formula (51) |
| 0.00017 | 99.4 | 102.4 | 97.5 | 97.0 |
| 0.00029 | 103.3 | 108.6 | 100.7 | 98.8 |
| 0.00039 | 106.4 | 111.2 | 102.7 | 97.7 |
| 0.00058 | 109.1 | 115.4 | 104.2 | 92.4 |
| 0.00078 | 110.4 | 117.0 | 103.9 | 87.7 |

*mol per 100 g of dry solid based on mol of 4,4'-diaminostilbene-2,2'-disulphonic acid per 100 g of dry solid

Application Example 4

A coating composition is prepared containing 700 parts chalk (commercially available under the trade name Hydrocarb 90 from OMYA), 300 parts clay (commercially available under the trade name Kaolin SPS from IMERYS), 428 parts water, 6 parts dispersing agent (a sodium salt of a polyacrylic acid commercially available under the trade name Polysalz S from BASF) and 200 parts of 50% latex (a styrene butadiene copolymer commercially available under the trade name DL 921 from Dow). The solids content of the coating composition is adjusted to approx. 65% by the addition of water, and the pH is adjusted to 8-9 with sodium hydroxide.

The so-formed coating composition is divided in small portions in which are added with stirring, aqueous solutions containing compounds of formula (21) and (51) respectively prepared according to example 21 and comparative example 2 at a concentration of from 0 to 0.0006 mol per 100 g of dry solid (mol being based on 4,4'-diaminostilbene-2,2'-disulphonic acid).

The brightened coating composition is then applied to a commercial 75 gsm neutral-sized white paper base sheet using an automatic wire-wound bar applicator with a standard speed setting and a standard load on the bar. The coated paper is then dried for 5 minutes in a hot air flow. Afterwards the paper is allowed to condition and measured then for CIE Whiteness on a calibrated Auto-Elrepho spectrophotometer. The results are shown in Table 4 and clearly show that the instant invention provides a higher level of whiteness.

TABLE 4

| Concentration (mol per 100 g of dry solid)* | Whiteness | |
|---|---|---|
| | Compound of formula (21) | Compound of formula (51) |
| 0 | 83.6 | 83.6 |
| 0.00023 | 98.5 | 98.3 |
| 0.00035 | 102.9 | 98.3 |
| 0.00046 | 105.8 | 95.1 |
| 0.00058 | 107.3 | 92.5 |

*mol per 100 g of dry solid based on mol of 4,4'-diaminostilbene-2,2'-disulphonic acid per 100 g of dry solid

The invention claimed is:

1. An optical brightening agent of formula (I)

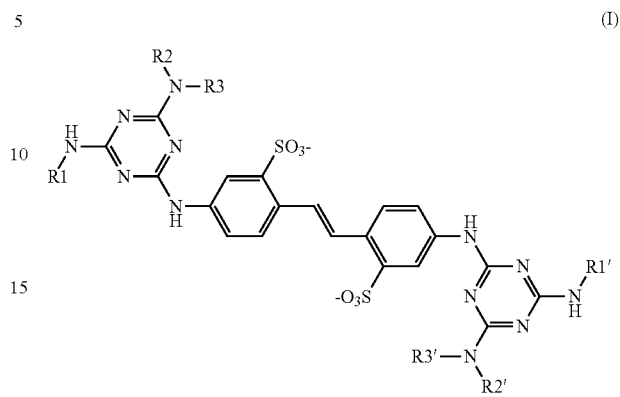

wherein
the anionic charge on the brightener is balanced by a cationic charge composed of one or more identical or different cations selected from the group consisting of hydrogen, an alkali metal cation, alkaline earth metal, ammonium, ammonium that is mono-, di-, tri- or tetrasubstituted by a $C_1$-$C_4$ linear or branched alkyl radical, ammonium that is mono-, di-, tri- or tetrasubstituted by a $C_1$-$C_4$ linear or branched hydroxyalkyl radical, ammonium that is, di-, tri- or tetrasubstituted by a mixture of $C_1$-$C_4$ linear or branched alkyl radical and linear or branched hydroxyalkyl radical, and mixtures thereof, R1 and R1' are the same or different and are each a radical of formula (II)

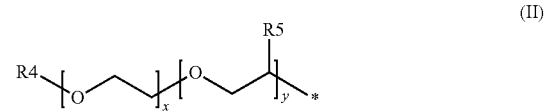

or R1 together with R1' are each a radical of formula (III)

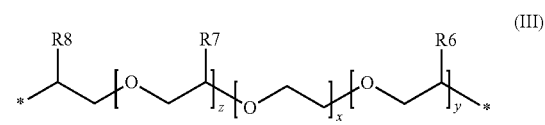

or R1 together with R1' are each a radical of formula (IV)

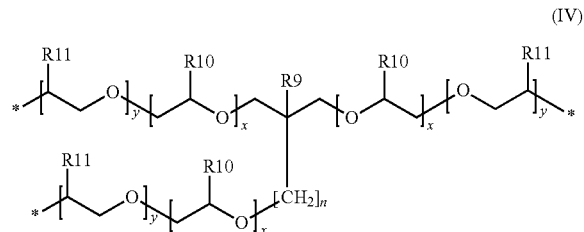

or mixtures thereof,
R2 and R2' are the same or different and are selected from the group consisting of hydrogen, $C_1$-$C_4$ linear or branched alkyl, $C_2$-$C_4$ linear or branched hydroxyalkyl, —$CH_2CO_2^-$, —$CH_2CH_2CONH_2$, and —$CH_2CH_2CN$,
or R2 and R2' are each a radical of formula (II)
or R2 together with R2' are each a radical of formula (III),
or R2 together with R2' are each a radical of formula (IV),
or R2 and R2' are each a radical of formula (V),

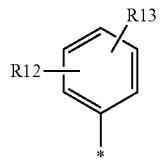

and mixtures thereof,
R3 and R3' are the same or different and are selected from the group consisting of hydrogen, $C_1$-$C_4$ linear or branched alkyl, $C_2$-$C_4$ linear or branched hydroxyalkyl, —$CH_2CO_2^-$, —$CH(CO_2^-)CH_2CO_2^-$, —$CH(CO_2^-)CH_2CH_2CO_2^-$, —$CH_2CH_2SO_3^-$, —$CH_2CH_2CO_2^-$, —$CH_2CH(CH_3)CO_2^-$, benzyl,
and mixtures thereof,
or R2 and R3 and/or R2' and R3' together with the neighboring nitrogen atom are each a morpholine, a piperidine, a piperazine, a pyrrole, or a pyrrolidine ring or mixtures thereof,
R12 and R13 are the same or different and are selected from the group consisting of hydrogen, $C_1$-$C_6$ linear or branched alkyl radical, halogen, —SR14, —OR15, —NR16R17, —CONR18R19, —COR20, —SO2NR21R22, —CN, —$CO_2^-$, —$SO_3^-$,
and mixtures thereof,
R4, R5, R6, R7, R8, R9, R10, R11, R14, R15, R16, R17, R18, R19, R20, R21 and R22 are the same or different and are selected from the group consisting of hydrogen, phenyl or $C_1$-$C_{25}$ linear and branched alkyl radical,
x, y, and z are the same or different and are each in the range of from 0 to 200, with the proviso that x+y+z≥5, if R1 together with R1' are each a radical of formula (III), or with the proviso that x+y≥5, if R1 and R1' are the same or different and are each a radical of formula (II), or R1 together with R1' are each a radical of formula (IV),
n is in the range of from 0 to 4,
or mixtures thereof.

2. The optical brightening agent according to claim 1, wherein in formula (I) the anionic charge is balanced by a cationic charge composed of one or more identical or different cations selected from the group consisting of hydrogen, Li, Na, K, Ca, Mg, ammonium, ammonium that is mono-, di-, tri- or tetrasubstituted by a $C_1$-$C_4$ linear or branched alkyl radical, ammonium that is mono-, di-, tri- or tetrasubstituted by a $C_1$-$C_4$ linear or branched hydroxyalkyl radical, ammonium that is, di-, tri- or tetrasubstituted by a mixture of $C_1$-$C_4$ linear or branched alkyl radical and linear or branched hydroxyalkyl radical, and mixtures thereof,
R1 and R1' are the same or different and are each a radical of formula (II)
or R1 together with R1' are each a radical of formula (III)
or R1 together with R1' are each a radical of formula (IV)
or mixtures thereof,
R2 and R2' are the same or different and are selected from the group consisting of hydrogen, methyl, ethyl, propyl, butyl, isopropyl, isobutyl, 2-hydroxyethyl, 2-hydroxypropyl, —$CH_2CO_2^-$, —$CH_2CH_2CONH_2$, and —$CH_2CH_2CN$,
or R2 and R2' are each a radical of formula (II)
or R2 together with R2' are each a radical of formula (III)
or R2 together with R2' are each a radical of formula (IV)
or R2 and R2' are each a radical of formula (V),
and mixtures thereof,
R3 and R3' are the same or different and are selected from the group consisting of hydrogen, methyl, ethyl, propyl, butyl, isopropyl, isobutyl, 2-hydroxyethyl, 2-hydroxypropyl, —$CH_2CO_2^-$, —$CH(CO_2^-)CH_2CO_2^-$, —$CH(CO_2^-)CH_2CH_2CO_2^-$, —$CH_2CH_2SO_3^-$, —$CH_2CH_2CO_2^-$, —$CH_2CH(CH_3)CO_2^-$, benzyl,
and mixtures thereof,
or R2 and R3 and/or R2' and R3' together with the neighboring nitrogen atom are each a morpholine, a piperidine or a pyrrolidine ring
or mixtures thereof,
R12 and R13 are the same or different and are selected from the group consisting of hydrogen, methyl, ethyl, propyl, isopropyl, butyl, isobutyl, 2-ethylhexyl, F, Cl, Br, I, —SR14, —OR15, —NR16R17, —CONR18R19, —COR20, —SO2NR21R22, —CN, —$CO_2^-$, —$SO_3^-$,
and mixtures thereof,
R4, R5, R6, R7, R8, R9, R10, R11, R14, R15, R16, R17, R18, R19, R20, R21 and R22 are the same or different and are selected from the group consisting of hydrogen, phenyl or $C_1$-$C_{20}$ and branched alkyl radical,
x, y, and z are the same or different and are each in the range of from 0 to 200, with the proviso that x+y+z≥5, if R1 together with R1' are each a radical of formula (III), or with the proviso that x+y≥5, if R1 and R1' are the same or different and are each a radical of formula (II), or R1 together with R1' are each a radical of formula (IV),
n is in the range of from 0 to 4,
or mixtures thereof.

3. The optical brightening agent according to claim 1, wherein in formula (I), the anionic charge is balanced by a cationic charge composed of one or more identical or different cations selected from the group consisting of hydrogen, Na, K, ammonium, triethanolamine, dimethylaminoethanol, and mixtures of said compounds thereof,
R1 and R1' are the same or different and are each a radical of formula (II)
or R1 together with R1' are each a radical of formula (III),
R2 and R2' are the same or different and are selected from the group consisting of hydrogen, methyl, ethyl, 2-hydroxyethyl, 2-hydroxypropyl, —$CH_2CO_2^-$, —$CH_2CH_2CONH_2$, and —$CH_2CH_2CN$,
or R2 and R2' are each a radical of formula (II)
or R2 together with R2' are each a radical of formula (III)
or R2 and R2' are each a radical of formula (V),
R3 and R3' are the same or different and are selected from the group consisting of methyl, ethyl, 2-hydroxyethyl, 2-hydroxypropyl, —$CH_2CO_2^-$, —$CH(CO_2^-)CH_2CO_2^-$, —$CH_2CH_2SO_3^-$,
and mixtures thereof,
or R2 and R3 and/or R2' and R3' together with the neighboring nitrogen atom are each a morpholine ring,
R12 and R13 are the same or different and are selected from the group consisting of hydrogen, —$CO_2^-$, and —$SO_3^-$,
R4, R5, R6, R7, R8, R9, R10, R11, R14, R15, R16, R17, R18, R19, R20, R21 and R22 are the same or different and are selected from the group consisting of hydrogen, $C_1$-$C_{20}$ linear, and branched alkyl radical,
x, y, and z are the same or different and are each in the range of from 0 to 150, with the proviso that x+y+z≥5, if R1 together with R1' are each a radical of formula (III), or with the proviso that x+y≥5, if R1 and R1' are the same or different and are each a radical of formula (II), or R1 together with R1' are each a radical of formula (IV), n is in the range of from 0 to 4, or mixtures thereof.

4. The optical brightening agent according to claim 1, wherein in formula (I), the anionic charge is balanced by a cationic charge composed of one or more identical or different cations selected from the group consisting of Na, K, dimethylaminoethanol, and mixtures thereof, R1 and R1' are each a radical of formula (II)

or R1 together with R1' are each a radical of formula (III)

R2 and R2' are each a radical of formula (II)

or R2 and R2' are each a radical of formula (V),

R3 and R3' are each hydrogen,

R12 and R13 are selected from the group consisting of hydrogen, $-CO_2^-$, and $-SO_3^-$, R4, R5, R6, R7, R8, R9, R10, R11, R14, R15, R16, R17, R18, R19, R20, R21 and R22 are selected from the group consisting of hydrogen and $C_1$-$C_{20}$ linear or branched alkyl radical, x, y, and z are the same or different and are each in the range of from 0 to 100, with the proviso that x+y+z≥5, if R1 together with R1' are each a radical of formula (III), or with the proviso that x+y≥5, if R1 and R1' are the same or different and are each a radical of formula (II), or R1 together with R1' are each a radical of formula (IV), n is in the range of from 0 to 4, or mixtures thereof.

5. A process for producing a compound of formula (I) according to claim 1, comprising stepwise reacting a cyanuric halide with an amine, a diamine, a triamine or mixtures of those amines, wherein the reacting comprising suspending the cyanuric halide in water, or in an aqueous/organic medium, introducing the amine without dilution, or in the form of an aqueous solution or suspension, substituting a first halogen of the cyanuric halide by a compound of formula (VI), (VII), (VIII), (IX), (X) or (XI),

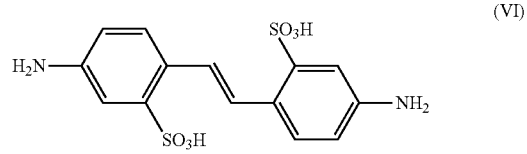

(VI)

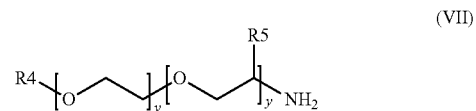

(VII)

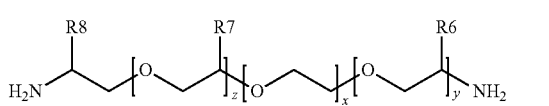

(VIII)

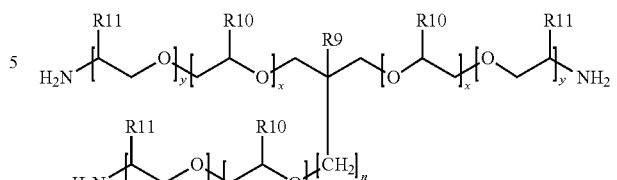

(IX)

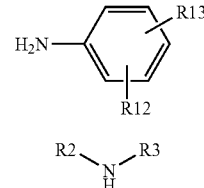

(X)

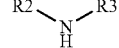

(XI)

x, y, and z are the same or different and are each in the range of from 0 to 100, with the proviso that x+y+z≥5, if R1 together with R1' are each a radical of formula (VIII), or with the proviso that x+y≥5, if R1 together with R1' are each a radical of formula (VII) or (IX), n is in the range of from 0 to 4, or mixtures thereof, wherein the substituting a first halogen is carried out at a temperature in the range of 0 to 20° C. and under acidic to neutral pH conditions, substituting a second halogen of the cyanuric halide by a compound of formula (VI), (VII), (VIII), (IX), (X) or (XI), wherein the substituting a second halogen is carried out at a temperature in the range of 20 to 60° C. and under weakly acidic to weakly alkaline conditions, and substituting a third halogen of the cyanuric halide by a compound of formula (VI), (VII), (VIII), (IX), (X) or (XI), wherein the substituting a third halogen is carried out at a temperature in the range of 60 to 102° C. and under weakly acidic to alkaline conditions.

6. A method comprising optical brightening a natural or regenerated cellulosic fibre, a natural or synthetic polyamide or a polyurethane fibre, a natural or synthetic pigment preparation, a textile and/or a paper comprising applying the optical brightening agent according to claim 1.

7. The method of claim 6, wherein a cellulose substrate is treated and wherein the agent of formula (I) is in an amount of from 0.00001 to 5% by weight based on the weight of a dry cellulosic substrate.

8. A method comprising treating a paper in a size-press, a sizing solution, and/or a suspension with the optical brightening agent according to claim 1, wherein said agent of formula (I) is in an amount of from 0.0001 to 125 grams per liter of the sizing solution and/or suspension.

9. A method comprising coating an object with a composition comprising a white pigment and the optical brightening agent according to claim 1, wherein said agent of formula (I) is in an amount from 0.00001 to 5% by weight based on the weight of the white pigment.

10. The optical brightening agent according to claim 1, wherein R5, R6, R7, R8, R10 and R11 are $CH_3$.

11. The optical brightening agent according to claim 1, wherein R5, R6, R7, R8, R10 and R11 are H.

12. The optical brightening agent according to claim 1, wherein R5, R6, R7, R8, R10 and R11 are a mixture of $CH_3$ and H.

13. A method comprising crease-proof finishing cotton comprising applying the optical brightening agent according to claim 1.

14. A coated article comprising at least one substrate selected from the group consisting of natural or regenerated cellulosic fibres, natural or synthetic polyamide or polyurethane fibres, natural or synthetic pigment preparations, textiles, and paper, wherein the at least one substrate is treated with the agent of claim 1.

15. The coated article according to claim 14, wherein the at least one substrate is paper.

16. The coated article according to claim 14, wherein the at least one substrate is natural or regenerated cellulosic fibres.

17. The optical brightening agent according to claim 1, wherein R1 together with R1' are each a radical of formula (II).

18. The optical brightening agent according to claim 1, wherein R1 together with R1' are each a radical of formula (III).

19. The optical brightening agent according to claim 1, wherein R1 together with R1' are each a radical of formula (IV).

20. The optical brightening agent according to claim 1, wherein R1 together with R1' are a mixture of radicals of formula (II), (III), and (IV).

\* \* \* \* \*